US009439978B2

(12) United States Patent
Mohapatra et al.

(10) Patent No.: US 9,439,978 B2
(45) Date of Patent: Sep. 13, 2016

(54) MULTILAYERED MAGNETIC MICELLE COMPOSITIONS AND METHODS FOR THEIR USE

(71) Applicants: Subhra Mohapatra, Lutz, FL (US); Chunyan Wang, Tampa, FL (US)

(72) Inventors: Subhra Mohapatra, Lutz, FL (US); Chunyan Wang, Tampa, FL (US)

(73) Assignees: University of South Florida, Tampa, FL (US); The United States of America as represented by National Institutes of Health (NIH), U.S. Dept. of Health and Human Services (DHHS), U.S. Government, Washington, DC (US)

( * ) Notice: Subject to any disclaimer, the term of this patent is extended or adjusted under 35 U.S.C. 154(b) by 0 days.

(21) Appl. No.: 14/346,330

(22) PCT Filed: Sep. 28, 2012

(86) PCT No.: PCT/US2012/057859
§ 371 (c)(1),
(2) Date: Mar. 21, 2014

(87) PCT Pub. No.: WO2013/049531
PCT Pub. Date: Apr. 4, 2013

(65) Prior Publication Data
US 2015/0064116 A1      Mar. 5, 2015

Related U.S. Application Data

(60) Provisional application No. 61/540,774, filed on Sep. 29, 2011, provisional application No. 61/602,391, filed on Feb. 23, 2012.

(51) Int. Cl.
| | |
|---|---|
| *A61K 48/00* | (2006.01) |
| *A61K 47/48* | (2006.01) |
| *A61K 49/18* | (2006.01) |
| *C12N 15/88* | (2006.01) |
| *C12N 15/85* | (2006.01) |

(52) U.S. Cl.
CPC ....... *A61K 48/0041* (2013.01); *A61K 47/4823* (2013.01); *A61K 47/48192* (2013.01); *A61K 47/48907* (2013.01); *A61K 47/48923* (2013.01); *A61K 48/0033* (2013.01); *A61K 49/1809* (2013.01); *A61K 49/1857* (2013.01); *A61K 49/1863* (2013.01); *A61K 49/1875* (2013.01); *C12N 15/85* (2013.01); *C12N 15/88* (2013.01); *C12N 2800/107* (2013.01); *C12N 2810/859* (2013.01)

(58) Field of Classification Search
CPC .. A61K 31/202; A61K 31/722; A61K 47/48; A61K 48/00; A61K 49/18
USPC ..................................................... 424/9.323
See application file for complete search history.

(56) References Cited

U.S. PATENT DOCUMENTS

| 6,824,780 B1 * | 11/2004 | Devaux .............. C07K 14/4748 424/156.1 |
|---|---|---|
| 2004/0096881 A1 | 5/2004 | Blasko |
| 2011/0002851 A1 | 1/2011 | Haas |
| 2011/0020239 A1 | 1/2011 | Bulte |
| 2011/0129525 A1 | 6/2011 | Rasschaert |

OTHER PUBLICATIONS

Dhananjay Jere et al., Chitosan-graft-polyethyleneimine for Akt1 siRNA delivery to lung cancer cells, International Journal of Pharmaceutics, 378, 194-200, 2009.*
Hua Ai et al., Magnetite-Loaded Polymeric Micelles as Ultrasensitive Magnetic-Resonace Probes, Advance Mater, 17, 1949-1952, 2005.*
Yuuka Fukui et al., The Preparation of Sugar Polymer-Coated Nanocapsule by the Layer-vy-Layer Deposition on the Liposome, Langmuir, 25(17), 10020-10025, 2009.*
Ragusa, A. et al. "Nanoparticles as nonviral gene delivery vectors" IEEE Transactions on Nanobioscience, 2007, vol. 6, No. 4, pp. 319-330.
Basarkar, A. et al. "Nanoparticulate systems for polynucleotide delivery" International Journal of Nanomedicine, 2007, vol. 2, No. 3, pp. 353-360.
International Search Report and Written Opinion mailed Mar. 26, 2013.
M. Breunig, U. Lungwitz, R. Liebl, A. Goepferich, Breaking up the correlation between efficacy and toxicity for nonviral gene delivery, Proc. Natl. Acad. Sci. U. S. A. 104 (2007) 14454-14459.
C.-H. Chang,W.-J. Cheng, S.-Y. Chen, M.-C. Kao, C.-J. Chiang, Y.-P. Chao, Engineering of *Escherichia coli* for targeted delivery of transgenes to HER2/neu-positive tumor cells, Biotechnol. Bioeng. 108 (2011).
G. Chen, W. Chen, Z. Wu, R. Yuan, H. Li, J. Gao, X. Shuai, MRI-visible polymeric vector bearing CD3 single chain antibody for gene delivery to T cells for immunosuppression, Biomaterials 30 (2009) 1962-1970.
R. Chen, H.I. Yu, Z.Y. Jia, Q.L. Yao, G.J. Teng, Efficient nano iron particle-labeling and noninvasive MR imaging of mouse bone marrow-derived endothelial progenitor cells, Int. J. Nanomedicine 6 (2011) 511-519.
Y.A. Chen, H.C. Kuo, Y.M. Chen, S.Y. Huang, Y.R. Liu, S.C. Lin, H.L. Yang, T.Y. Chen, A gene delivery system based on the N-terminal domain of human topoisomerase I, Biomaterials 32 (2011) 4174-4184.

(Continued)

*Primary Examiner* — Michael G Hartley
*Assistant Examiner* — Jagadishwar Samala
(74) *Attorney, Agent, or Firm* — Thomas | Horstemeyer, LLP

(57) ABSTRACT

Provided herein are compositions comprising a micelle having a hydrophobic superparmagnetic iron oxide nanoparticle (SPION) core, a first coating comprising a cationic polymer, and a second coating comprising a polynucleotide. Also provided are methods of using the compositions for transfection and/or transformation of a cell with the polynucleotide. Further provided are methods of detecting transfection of a cell with the polynucleotide.

30 Claims, 24 Drawing Sheets

(56) References Cited

OTHER PUBLICATIONS

D. Cheng, G.B. Hong, W.W. Wang, R.X. Yuan, H. Ai, J. Shen, B.L. Liang, J.M. Gao, X.T. Shuai, Nonclustered magnetite nanoparticle encapsulated biodegradable polymeric micelles with enhanced properties for in vivo tumor imaging, J. Mater. Chem. 21 (2011) 4796-4804.

L.Y.T. Chou, K. Ming, W.C.W. Chan, Strategies for the intracellular delivery of nanoparticles, Chem. Soc. Rev. 40 (2011) 233-245.

M. Conese, F. Ascenzioni, A.C. Boyd, C. Coutelle, I. De Fino, S. de Smedt, J. Rejman, J. Rosenecker, D. Schindelhauer, B.J. Scholte, Gene and cell therapy for cystic fibrosis: from bench to bedside, J. Cyst. Fibros. 10 (2011) S114-S128.

K. Corsi, F. Chellat, L. Yahia, J.C. Fernandes, Mesenchymal stem cells, MG63 and HEK293 transfection using chitosan-DNA nanoparticles, Biomaterials 24 (2003) 1255-1264.

T. Dastan, K. Turan, In vitro characterization and delivery of chitosan-DNA microparticles into mammalian cells, J. Pharm. Pharm. Sci. 7 (2004) 205-214.

J. Dennig, Gene transfer in eukaryotic cells using activated dendrimers, Dendrimers V: Functional and Hyperbranched Building Blocks, Photophysical Properties, Applications in Materials and Life Sciences, 228, 2003, pp. 227-236.

H. Duan, S. S Nie, Cell-penetrating quantum dots based on multivalent and endosomolytic surface coatings, Abstr. Pap. Am. Chem. Soc. 233 (2007).

P. Dutta, S. Pal, M.S. Seehra, N. Shah, G.P. Huffman, Size dependence of magnetic parameters and surface disorder in magnetite nanoparticles, J. Appl. Phys. 105 (2009) 07B501/1-3.

M.L. Edelstein, M.R. Abedi, J. Wixon, Gene therapy clinical trials worldwide to 2007—an update, J. Gene Med. 9 (2007) 833-842.

G.H. Gao, G.H. Im, M.S. Kim, J.W. Lee, J. Yang, H. Jeon, J.H. Lee, D.S. Lee, Magnetite-nanoparticle-encapsulated pH-responsive polymeric micelle as an MRI probe for detecting acidic pathologic areas, Small 6 (2010) 1201-1204.

L.Z. Gao, L. Nie, T.H. Wang, Y.J. Qin, Z.X. Guo, D.L. Yang, X.Y. Yan, Carbon nanotube delivery of the GFP gene into mammalian cells, Chembiochem 7 (2006) 239-242.

J.F. Guo, L. Bourre, D.M. Soden, G.C. O'Sullivan, C. O'Driscoll, Can non-viral technologies knockdown the barriers to siRNA delivery and achieve the next generation of cancer therapeutics? Biotechnol. Adv. 29 (2011) 402-417.

J.S. Guthi, S.G. Yang, G. Huang, S.Z. Li, C. Khemtong, C.W. Kessinger, M. Peyton, J.D. Minna, K.C. Brown, J.M. Gao, MRI-visible micellar nanomedicine for targeted drug delivery to lung cancer cells, Mol. Pharm. 7 (2010) 32-40.

G. Han, N.S. Chari, A. Verma, R. Hong C.T. Martin, V.M. Rotello, Controlled recovery of the transcription of nanoparticle-bound DNA by intracellular concentrations of glutathione, Bioconjug. Chem. 16 (2005) 1356-1359.

G. Han, C.T. Martin, V.M. Rotello, Stability of gold nanoparticle-bound DNA toward biological, physical, and chemical agents, Chem. Biol. Drug Des. 67 (2006) 78-82.

G.B. Hong, R.X. Yuan, B.L. Liang, J. Shen, X.Q. Yang, X.T. Shuai, Folate-functionalized polymeric micelle as hepatic carcinoma-targeted, MRI-ultrasensitive delivery system of antitumor drugs, Biomed. Microdevices 10 (2008) 693-700.

D. Jere, H.L. Jiang, Y.K. Kim, R. Arote, Y.J. Choi, C.H. Yun, M.H. Cho, C.S. Cho, Chitosangraft-polyethylenimine for Akt1 siRNA delivery to lung cancer cells, Int. J. Pharm. 378 (2009) 194-200.

H.L. Jiang, J.T. Kwon, Y.K. Kim, E.M. Kim, R. Arote, H.J. Jeong, J.W. Nah, Y.J. Choi, T. Akaike, M.H. Cho, C.S. Cho, Galactosylated chitosan-graft-polyethylenimine as a gene carrier for hepatocyte targeting, Gene Ther. 14 (2007) 1389-1398.

H.L. Jiang, Y.K. Kim, R. Arote, J.W. Nah, M.H. Cho, Y.J. Choi, T. Akaike, C.S. Cho, Chitosan-graft-polyethylenimine as a gene carrier, J. Control. Release 117 (2007) 273-280.

H.L. Jiang, J.T. Kwon, E.M. Kim, Y.K. Kim, R. Arote, D. Jere, H.J. Jeong, M.K. Jang, J.W.Nah, C.X. Xu, I.K. Park, M.H. Cho, C.S. Cho, Galactosylated poly(ethylene glycol)-chitosan-graft-polyethylenimine as a gene carrier for hepatocyte-targeting, J. Control. Release 131 (2008) 150-157.

C.W. Jiang, P. Jacobs, Physical and chemical-properties of superparamagnetic ironoxide MR contrast agents ferumoxides, ferumoxtran, ferumoxsil, Magn. Reson. Imaging 13 (1995) 661-674.

T.L. Kaneshiro, X. Wang, Z.R. Lu, Synthesis, characterization, and gene delivery of Poly-L-lySine octa(3-aminopropyl) silsesquioxane dendrimers: nanoglobular drug carriers with precisely defined molecular Architectures, Mol. Pharm. 4 (2007) 759-768.

F.M. Kievit, O. Veiseh, N. Bhattarai, C. Fang, J.W. Gunn, D. Lee, R.G. Ellenbogen, J.M. Olson, M.Q. Zhang, PEI-PEG-chitosan-copolymer-coated iron oxide nanoparticles for safe gene delivery: synthesis, complexation, and transfection, Adv. Funct. Mater. 19 (2009) 2244-2251.

J.R. Lai, Y.W. Chang, H.C. Yen, N.Y. Yuan, M.Y. Liao, C.Y. Hsu, J.L. Tsai, P.S. Lai, Multifunctional doxorubicin/superparamagnetic iron oxide-encapsulated Pluronic F127 micelles used for chemotherapy/magnetic resonance imaging, J. Appl. Phys. 107 (2010).

P.-W. Lee, S.-H. Hsu, J.-J. Wang, J.-S. Tsai, K.-J. Lin, S.-P. Wey, F.-R. Chen, C.-H. Lai, T.-C. Yen, H.-W. Sung, The characteristics, biodistribution, magnetic resonance imaging and biodegradability of superparamagnetic core-shell nanoparticles, Biomaterials 31 (2010) 1316-1324.

E.S. Lee, K. Na, Y.H. Bae, Polymeric micelle for tumor pH and folate-mediated targeting, J. Control. Release 91 (2003) 103-113.

Y.L. Lou, Y.S. Peng, B.H. Chen, L.F. Wang, K.W. Leong, Poly(ethylene imine)-gchitosan using EX-810 as a spacer for nonviral gene delivery vectors, J. Biomed. Mater. Res. A 88A (2009) 1058-1068.

A. Lucke, J. Tessmar, E. Schnell, G. Schmeer, A. Gopferich, Biodegradable poly(D, Llactic acid)-poly(ethylene glycol)-monomethyl ether diblock copolymers: structures and surface properties relevant to their use as biomaterials, Biomaterials 21 (2000) 2361-2370.

U. Lungwitz, M. Breunig, T. Blunk, A. Gopferich, Polyethylenimine-based non-viral gene delivery systems, Eur. J. Pharm. Biopharm. 60 (2005) 247-266.

C.M. McIntosh, E.A. Esposito, A.K. Boal, J.M. Simard, C.T. Martin, V.M. Rotello, Inhibition of DNA transcription using cationic mixed monolayer protected gold clusters, J. Am. Chem. Soc. 123 (2001) 7626-7629.

M. Morille, C. Passirani, A. Vonarbourg, A. Clavreul, J.P. Benoit, Progress in developing cationic vectors for non-viral systemic gene therapy against cancer, Biomaterials 29 (2008) 3477-3496.

O. Mykhaylyk, Y.S. Antequera, D. Vlaskou, C. Plank, Generation of magnetic nonviral gene transfer agents and magnetofection in vitro, Nat. Protoc. 2 (2007) 2391-2411.

N. Nasongkla, E. Bey, J.M. Ren, H. Ai, C. Khemtong, J.S. Guthi, S.F. Chin, A.D. Sherry, D.A. Boothman, J.M. Gao, Multifunctional polymeric micelles as cancer-targeted, MRI-ultrasensitive drug delivery systems, Nano Lett. 6 (2006) 2427-2430.

X.T. Shuai, H. Ai, N. Nasongkla, S. Kim, J.M. Gao, Micellar carriers based on block copolymers of poly(e-caprolactone) and poly(ethylene glycol) for doxorubicin delivery, J. Control. Release 98 (2004) 415-426.

S.H. Sun, H. Zeng, Size-controlled synthesis of magnetite nanoparticles, J. Am. Chem. Soc. 124 (2002) 8204-8205.

C.E. Thomas, A. Ehrhardt, M.A. Kay, Progress and problems with the use of viral vectors for gene therapy, Nat. Rev. Genet. 4 (2003) 346-358.

D.L.J. Thorek, A. Chen, J. Czupryna, A. Tsourkas, Superparamagnetic iron oxide nanoparticle probes for molecular imaging, Ann. Biomed. Eng. 34 (2006) 23-38.

O. Veiseh, F.M. Kievit, C. Fang, N. Mu, S. Jana, M.C. Leung, H. Mok, R.G. Ellenbogen, J.O. Park, M. Zhang, Chlorotoxin bound magnetic nanovector tailored for cancer cell targeting, imaging, and siRNA delivery, Biomaterials 31 (2010).

Y.X.J. Wang, S.M. Hussain, G.P. Krestin, Superparamagnetic iron oxide contrast agents: physicochemical characteristics and applications in MR imaging, Eur. Radiol. 11 (2001) 2319-2331.

K. Wong, G.B. Sun, X.Q. Zhang, H. Dai, Y. Liu, C.B. He, K.W. Leong, PEI-g-chitosan, a novel gene delivery system with transfec-

(56) References Cited

OTHER PUBLICATIONS tion efficiency comparable to polyethylenimine in vitro and after liver administration in vivo, Bioconjug. Chem. 17 (2006) 152-158.
H.M. Wu, S.R. Pan, M.W. Chen, Y. Wu, C. Wang, Y.T. Wen, X. Zeng, C.B. Wu, A serum-resistant polyamidoamine-based polypeptide dendrimer for gene transfection, Biomaterials 32 (2011) 1619-1634.
P. Zou, Y.K. Yu, Y.A. Wang, Y.Q. Zhong, A. Welton, C. Galban, S.M. Wang, D.X. Sun, Superparamagnetic iron oxide nanotheranostics for targeted cancer cell imaging and pH-dependent intracellular drug release, Mol. Pharm. 7 (2010) 1974-1984.
H.L. Jiang, M. Nagaoka, Y.K. Kim, R. Arote, D. Jere, I.Y. Park, T. Akaike, C.S. Cho, Gene delivery to stem cells by combination of chitosan-graft-polyethylenimine as a gene carrier and E-cadherin-IgG Fc as an extracellular matrix, J. Biomed. Nanotechnol. 3 (2007) 377-383.
Miller, Carin R. Response letter to USPTO Examiner, Response to Non Final Office Action mailed Jan. 7, 2016, U.S. Appl. No. 13/773,718, filed Feb. 22, 2013.
Wang C, Ravi S, Martinez GV, Chinnsamy V, Raulji P, Howell M, Davis Y, Mallela J, Seehra MS, Mohapatra S (2012) Dual-purpose magnetic micelles for MRI and gene delivery. J Control Release, 163 (2012) 82-92.
M. Das et al., Lateral fluid percussion injury of the brain induces CCL20 inflammatory chemokine expression in rats. Journal of Neuroinflammation 2011, 8, 148.
Schmued LC, Albertson C, Slikker W, Jr. (1997) Fluoro-Jade: a novel fluorochrome for the sensitive and reliable histochemical localization of neuronal degeneration. Brain Res 751:37-46.
E. A. Duckworth et al., Temporary focal ischemia in the mouse: technical aspects and patterns on Fluoro-Jade evident neurodegeneration. Brain Research 2005, 1042, 29-36.
Al-Deen, F.N., et al., On designing stable magnetic vectors as carriers for malaria DNA vaccine, Colloids Surf B Biointerfaces, Feb. 1, 2013, 102C:492-503.
Al-Deen, F.N., et al., Superparamagnetic nanoparticles for effective delivery of malaria DNA vaccine. Langmuir, 2011, 27:7, 3703-3712.
Castillo, B., et al., Intracellular Delivery of siRNA by Polycationic Superparamagnetic Nanoparticles, J Drug Deliv., 2012, 2012:218940.
Cho, Y., et al., Chitosan produces potent neuroprotein and physiological recovery following traumatic spinal cord injury. J Exp. Biol., 2010, 213:1513-1520.
Dalby, B., et al., 2004, Advanced transfection with Lipofectamine 2000 reagent: primary neurons, siRNA, and high-throughput applications, Methods 22:95-103.
Ettenhofer, M. L., et al., A Comparison of Long-Term Postconcussive Symptoms between University Students with and without a History of Mild Traumatic Brain Injury or Orthopedic injury. J. Int. Neuropsychol. Soc., May 2012, 18:3, 1-10.
Ettenhofer, M. L., et al., 2009, The significance of mild traumatic brain injury to cognition and self-reported symptoms in long-term recovery from injury. J. Clin. Exp. Neuropsychol. 31:363-372.
Faul, M., et al., 2010, Traumatic brain injury in the United States: emergency department visits, hospitalizations, and deaths. Atlanta (GA): Centers for Disease Control and Prevention, National Center for injury Prevention and Control, Mar. 2010.
Gersting, S. W., et al., 2004, Gene delivery to respiratory epithelial cells by magnetofection. J. Gene Med. 6:913-922.
Guerra-Crespo, M., et al., 2003, Polyethylenimine improves the transfection efficiency of primary cultures of post-mitotic rat fetal hypothalamic neurons. J Neurosci Methods 127: 179-192.
Halldorsson J. G., et al., The scope of early traumatic brain injury as a long-term health concern in two nationwide samples: prevalence and prognostic factors. Brain Inj., 2012, 26:1, 1-13.
Kabadi, S. V., et al., 2010, Fluid-percussion-induced-traumatic brain injury model in rats. Nature protocols 5:1552-1563.
McBain S. C., et al., 2008, Magnetic nanoparticles as gene delivery agents: enhanced transfection in the presence of oscillating magnet arrays, Nanotechnology 19:405102.
Ozen, L. J., et al., 2012, Slowing down after a mild traumatic brain injury: a strategy to improve cognitive task performance? Arch Clin Neuropsychol 27:85-100.
Perez-Martinez, F. C., et al., 2009, Barriers to non-viral vector-mediated gene delivery in the nervous system. Pharm Res 28:1843-1858.
Plank C, Vlaskou D, Schillinger U, Mykhaylyk O., 2011, MagnetofectionTM platform: from magnetic nanopaticles to novel nucleic acid therapeutics. Ther Deliv 2:717-726.
Plank C, Anton M, Rudolph C, Rosenecker J, Krotz F (2003) Enhancing and targeting nucleic acid delivery by magnetic force. Expert Opin Biol Ther 3:745-758.
Plank C, Schillinger U, Scherer F, Bergemann C, Remy JS, Krotz F, Anton M, Lausier J, Rosenecker J (2003) The magnetofection method: using magnetic force to enhance gene delivery. Biol Chem 384:737-747.
Schwerdt JI, Goya GF, Calatayud MP, Herenu CB, Reggiani PC, Goya RG (2012) Magnetic feld-assisted gene delivery: achievements and therapeutic potential. Curr Gene Ther 12:116-126.
Vainauska D, Kozireva S, Karpovs A, Cistjakovs M, Barisevs M (2012) A novel approach for nucleic acid delivery into cancer cells. Medicina (Kaunas) 48:324-329.
Yang SY, Sun JS, Liu CH, Tsuang YH, Chen LT, Hong CY, Yang HC, Horng HE (2008) Ex vivo magnetofection with magnetic nanoparticles: a novel platform for nonviral tissue engineering. Artif Organs 32:195-204.
Yun J, Sonabend AM, Ulasov IV, Kim DH, Rozhkova EA, Novosad V, Dashnaw S, Brown T, Canoll P, Bruce JN, Lesniak MS (2012) A novel adenoviral vector labeled with superparamagnetic iron oxide nanoparticies for real-time tracking of viral delivery. J Clin Neurosci 19:875-880.
Hua Ai et al., Magnetite-Loaded Polymeric Miceles as Ultrasensitive Magnetic-Resonance Probes, Advanced Mater, 17, 1949-1952, 2005.

\* cited by examiner

Step 1

DC= 1,2-dodecanediol ; OA=oleic acid ; OL= oleylamine, BE= benzyl ether;

Step 2

Step 3

| micelles | Pd% |
|---|---|
| Mag-micelle | 9.3 |
| CS-mag-micelle | 17.1 |
| CP-mag-micelle(7:3) | 7.6 |
| CP-mag-micelle(5:5) | 7.5 |
| CP-mag-micelle(3:7) | 13.4 |
| DNA-CS-mag-micelle | 43.9 |
| DNA-CP-mag-micelle(7:3) | 9.7 |
| DNA-CP-mag-micelle(5:5) | 11.5 |
| DNA-CP-mag-micelle(3:7) | 26.3 |

FIG. 23

MULTILAYERED MAGNETIC MICELLE COMPOSITIONS AND METHODS FOR THEIR USE

CROSS-REFERENCE TO RELATED APPLICATION

This application is the 35 U.S.C. §371 national stage of, and claims priority to and the benefit of, PCT application PCT/US2012/057859, filed Sep. 28, 2012, which claims priority to and the benefit of U.S. Provisional Application No. 61/540,774, filed on Sep. 29, 2011, and claims priority to and the benefit of U.S. Provisional Application No. 61/602,391, filed on Feb. 23, 2012 herein incorporated by reference in their entirety.

STATEMENT AS TO RIGHTS TO INVENTIONS MADE UNDER FEDERALLY SPONSORED RESEARCH AND DEVELOPMENT

This invention was made with government support under the National Institutes of Health Grants R41CA139785 and 5R01CA152005. The U.S. government has certain rights in this invention.

BACKGROUND

Gene therapy is used to treat hereditary diseases such as cystic fibrosis and also acquired diseases such as cancers [M. Conese, et al., Journal of Cystic Fibrosis (2011) 10, S114], but is only as effective as its ability to deliver the therapeutic polynucleotide to a desired location. Vectors for gene delivery may be viral or nonviral. Viral vectors offer highly efficient gene transfer, but unwanted immune stimulation and the potential for mutagenesis have virtually eliminated them from clinical trials [M. L. Edelstein, et al., Journal of Gene Medicine (2007) 9, 833; C. E. Thomas, et al., Nature Reviews Genetics (2003) 4, 346]. In contrast, nonviral vectors are safe, have low immunogenicity, and are relatively inexpensive [J. F. Guo, et al., Biotechnology Advances (2011) 29, 402].

Examples of nonviral vectors include bacteria [C. H. Chang, et al., Biotechnology and Bioengineering 2011, 108], cell penetrating peptides [Y. A. Chen, et al., Biomaterials 2011, 32, 4174], functionalized gold nanoparticles or carbon nanotubes [C. M. McIntosh, et al., Journal of the American Chemical Society 2001, 123, 7626; G. Han, et al., Chemical Biology & Drug Design 2006, 67, 78; G. Han, et al., Bioconjugate Chemistry 2005, 16, 1356; L. Z. Gao, et al., Chembiochem 2006, 7, 239], and cationic polymers. Among these nonviral vectors, cationic polymers including polyethyleneimine (PEI) [U. Lungwitz, et al., Eur. J. of Pharmaceutics and Biopharmaceutics 2005, 60, 247], poly(1-lysine) (PLL) [U. Lungwitz, et al., Eur. J. of Pharmaceutics and Biopharmaceutics 2005, 60, 247; T. L. Kaneshiro, et al., Molecular Pharmaceutics 2007, 4, 759], chitosan [K. Corsi, et al., Biomaterials 2003, 24, 1255], dendrimers 9J. Dennig, Dendrimers V: Functional and Hyperbranched Building Blocks, Photophysical Properties, Applications in Materials and Life Sciences 2003, 228, 227; H. M. Wu, et al., Biomaterials 2011, 32, 1619] and cationic lipids [M. Morille, et al., Biomaterials 2008, 29, 3477] have the advantages of being scalable for manufacturing in quantity, having low immunogenicity, the capacity for selective chemical modification and the ability to carry large inserts. Due to its superior transfection efficiency in a broad range of cell types, synthetic PEI has a privileged place among nonviral gene delivery systems. However, the high number of positive charges on PEI and its lack of biodegradability make it toxic in vivo and has thus hampered clinical applications [U. Lungwitz, et al., Eur. J. of Pharmaceutics and Biopharmaceutics 2005, 60, 247; T. L. Kaneshiro, et al., Molecular Pharmaceutics 2007, 4, 759].

Chitosan, which is obtained by deacetylation of chitin, is a biocompatible and biodegradable linear polymer whose cationic polyelectrolyte nature provides strong electrostatic interaction with negative charged DNA to form stable complexes that protect the DNA from degradation. However, the transfection efficiency of chitosan is very low and is dependent on its molecular weight, size and percentage of deacetylation [H. L. Jiang, et al., Journal of Controlled Release 2007, 117, 273]. The goal of a successful nonviral gene delivery system, therefore, is to achieve therapeutic efficacy while minimizing toxicity [M. Breunig, et al., Proceedings of the National Academy of Sciences of the United States of America 2007, 104, 14454]. To develop such a safe and effective delivery vehicle, PEI-grafted chitosan, chitosan-grafted PEI or a chitosan-PEI composite have been tested and shown to have improved transfection efficiency and reduced toxicity compared to PEI alone [Y. L. Lou, et al., Journal of Biomedical Materials Research Part A 2009, 88A, 1058; D. Jere, et al., International Journal of Pharmaceutics 2009, 378, 194; H. L. Jiang, et al., Gene Therapy 2007, 14, 1389; H. L. Jiang, et al., Journal of Biomedical Nanotechnology 2007, 3, 377].

For advanced gene therapy, it is desirable to be able to monitor the in-vivo gene delivery in real time. Magnetic resonance imaging (MRI) is a powerful clinical imaging technique for diagnosis of a variety of diseases and post-therapy assessment. MRI contrast can be enhanced by the use of positive or negative contrast agents resulting in brighter (T1-weighted) or darker (T2-weighted) images, respectively. Superparamagnetic iron oxide nanoparticles (SPIONs) are T2 contrast agents that are widely used in molecular and cellular imaging applications [P. Zou, et al. Sun, Molecular Pharmaceutics 2010, 7, 1974; R. Chen, et al., International Journal of Nanomedicine 2011, 6, 511]. Recently, PEI-poly(ethylene glycol) (PEG)-chitosan coated SPIONs have been reported for DNA or siRNA delivery and MRI imaging [F. M. Kievit, et al., Advanced Functional Materials 2009, 19, 2244; O. Veiseh, et al., Biomaterials 2010, 31] and PEG-grafted PEI-complexed SPION for gene delivery and MRI imaging [G. Chen, et al., Biomaterials 2009, 30, 1962]. When incorporated into micelles, a SPION has a longer half-life in circulation, improved biocompatibility, and shows better contrast. SPION polymeric micelles were used successfully as MRI probes and for drug delivery [N. Nasongkla, et al., Nano Letters 2006, 6, 2427; X. T. Shuai, et al., Journal of Controlled Release 2004, 98, 41; J. S. Guthi, et al., Molecular Pharmaceutics 2010, 7, 32; G. B. Hong, et al. Biomedical Microdevices 2008, 10, 693], but they have not been tested for gene delivery.

BRIEF DESCRIPTION OF THE DRAWINGS

FIG. 23 provides a Table that shows the polydispersity index (Pd %) of mag-micelles detected by DLS.

DETAILED DESCRIPTION

Figure 1:
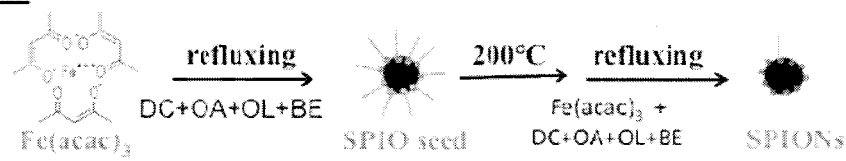
FIG. 1 shows a schematic illustration of the 4M-NP synthesis.
Figure 1:
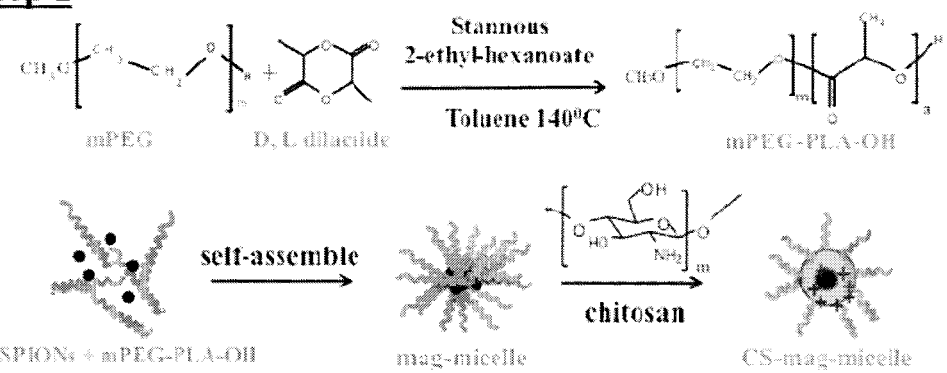
Figure 1:
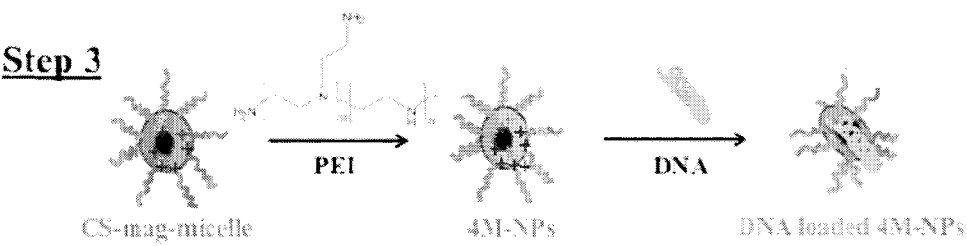

Described herein is a theranostic system including multilayered multimodal magnetic micelle nanoparticles produced by coating SPION-loaded micelles with cationic polymers, such as chitosan and PEI. These nanoparticles were characterized by transmission electron microscopy (TEM), dynamic light scattering (DLS), Fourier transform infrared (FTIR) spectrometry and nuclear magnetic resonance (NMR). The ability of these magnetic micelle nanoparticles to deliver DNA for gene expression while maintaining superparamagnetic properties and high biocompatibility, is shown through DNA binding assays, transfection studies in various cell lines, MR phantom imaging, biodistribution, in-vivo gene expression, and toxicity studies.

Term definitions used in the specification and claims are as follows:

DEFINITIONS

As used in the specification and claims, the singular form "a", "an" and "the" include plural references unless the context clearly dictates otherwise. For example, the term "a cell" includes a plurality of cells, including mixtures thereof.

The term "active derivative" and the like means a modified chitosan, PEI composition that retains an ability to both protect a polynucleotide and allow for its expression once inside a cell. Assays for testing the ability of an active derivative to perform in this fashion are provided herein.

When referring to a subject or patient, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-peritoneal, intra-synovial, intrasternal, intrathecal, intrahepatic, intralesional, and intracranial injections or infusion techniques. Is some embodiments, the administration is intravenous.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. An antibody "specific for" another substance binds, is bound by, or forms a complex with that substance.

The term "antibody fragment" refers to a portion of a full-length antibody, generally the target binding or variable region. Examples of antibody fragments include Fab, Fab', $F(ab')_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcϵRI. As used herein, "functional fragment" with respect to antibodies, refers to Fv, F(ab) and $F(ab')_2$ fragments. The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

As used herein, the terms "cancer", "cancer cells", "neoplastic cells", "neoplasia", "tumor", and "tumor cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor. In some embodiments, the cancer is prostate cancer.

The terms "cell", "cell line" and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

It should be understood that the term "coating" does not require a complete coverage of the coated object and that partial coverage is encompassed by the term.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "effective amount" is an amount sufficient to effect beneficial or desired results. An effective amount can be administered in one or more administrations, applications or dosages.

As used herein, "expression" refers to the process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in an eukaryotic cell. "Overexpression" as applied to a gene, refers to the overproduction of the mRNA transcribed from the gene or the protein product encoded by the gene, at a level that is 2.5 times higher, preferably 5 times higher, more preferably 10 times higher than the expression level detected in a control sample.

A "gene" refers to a polynucleotide containing at least one open reading frame that is capable of encoding a particular polypeptide or protein after being transcribed and translated. Any of the polynucleotides sequences described herein may be used to identify larger fragments or full-length coding sequences of the gene with which they are associated.

Methods of isolating larger fragment sequences are known to those of skill in the art, some of which are described herein.

A "gene product" refers to the amino acid (e.g., peptide or polypeptide) generated when a gene is transcribed and translated.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

The term "isolated" means separated from constituents, cellular and otherwise, in which the polynucleotide, peptide, polypeptide, protein, antibody, or fragments thereof, are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

As used herein, the term "micelle" refers to an aggregation of molecules wherein hydrophobic portions of the molecules comprise the interior of the aggregation and hydrophilic portions of the molecules comprise the exterior of the aggregation.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well-known techniques. The parent monoclonal antibodies to be used in accordance with the present invention may be made by the hybridoma method or may be made by recombinant methods.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives.

The term "pharmaceutically acceptable salts" refers to any acid or base addition salt whose counter-ions are non-toxic to the subject to which they are administered in pharmaceutical doses of the salts. Specific examples of pharmaceutically acceptable salts are provided below.

The terms "pharmaceutically effective amount", "therapeutically effective amount" or "therapeutically effective dose" refer to the amount of a compound that will elicit the biological or medical response of a tissue, system, animal, or human that is being sought by the researcher, veterinarian, medical doctor or other clinician.

The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or conditions and its severity, the route of administration, time of administration, rate of excretion, drug combination, judgment of the treating physician, dosage form, and the age, weight, general health, sex and/or diet of the subject to be treated.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, polynucleotide probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

"Selectively binds" refers to a non-specific binding event as determined by an appropriate comparative control. Binding is selective when the binding is at least 10, 30, or 40 times greater than that of background binding in the comparative control.

A "subject," "individual" or "patient" is used interchangeably herein, which refers to a vertebrate, preferably a mammal, more preferably a human. Mammals include, but are not limited to, murines, simians, humans, farm animals, sport animals, and pets.

"Transformation" of a cellular organism with DNA means introducing DNA into an organism so that the DNA is replicable, either as an extrachromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of *E. coli*. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

Accordingly, provided herein is a composition comprising a micelle having a superparamagnetic iron oxide nanoparticle (SPION) core, a first coating comprising one or more cationic polymers, and a second coating comprising a polynucleotide. Some embodiments of this composition are referred to herein as 4M-NPAs. The cationic polymers found in the first coating include, but are not limited to, chitosan, polyethyleneimine (PEI), poly(1-lysine) (PLL), dendrimers, and cationic lipids. In some embodiments, the first coating comprises chitosan, wherein chitosan has a chemical formula of:

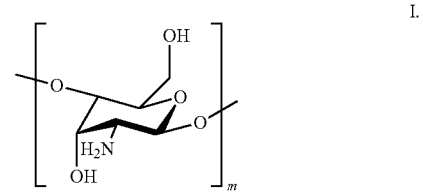

I.

wherein m is between 1 and 10,000, or an active derivative thereof. In other or further embodiments, the first coating comprises PEI, wherein PEI has a chemical formula of:

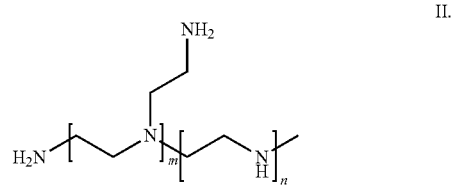

II.

wherein m is between 1 and 10,000, and n is between 1 and 10,000, or an active derivative thereof.

The chitosan, PEI and polynucleotide can be in any amount. However, in some embodiments, the polynucleotide is at a concentration between approximately 1 and 3 µg/ml (including approximately 1 µg/ml, 2 µg/ml and 3 µg/ml). In further or other embodiments, the molar weight ratio of chitosan and polynucleotide is between approximately 3:1 and 7:1. In still further or other embodiments, the molar weight ratio of PEI and polynucleotide is between approximately 7:1 and 3:1. In yet further or other embodiments, the molar weight ratio of chitosan and PEI is between approximately 3:7 and 7:3. Accordingly, provided herein are compositions comprising a micelle having a superparamagnetic iron oxide nanoparticle (SPION) core, a first coating comprising chitosan and PEI, and a second coating comprising a polynucleotide, wherein the chitosan/PEI/polynucleotide molar weight ratio is between approximately 3:3:1 and 7:7:1, and includes chitosan/PEI/polynucleotide molar weight ratios of approximately 3:7:1, 7:3:1, and 5:5:1.

Accordingly, in some embodiments the composition comprises a micelle having a superparamagnetic iron oxide nanoparticle (SPION) core, a first coating comprising chitosan having the chemical formula of I and PEI having the chemical formula of II, and a second coating comprising a polynucleotide. In one embodiment, the composition comprises a micelle having a superparamagnetic iron oxide nanoparticle (SPION) core, a first coating comprising chitosan having the chemical formula of I wherein m is between approximately 1 and 10,000, and PEI having the chemical formula of II wherein m is between approximately 1 and 10,000 and n is between approximately 1 and 10,000, and a second coating comprising a polynucleotide.

The term micelle is used herein to refer to an aggregation of molecules wherein hydrophilic portions of the molecules comprise the interior of the aggregation and hydrophobic portions of the molecules comprise the exterior of the aggregation. In some embodiments the molecules that comprise the micelle are copolymers of polyethylene glycol and poly D, L-dilactide. In certain further embodiments, the molecules that comprise the micelle have the chemical formula of III:

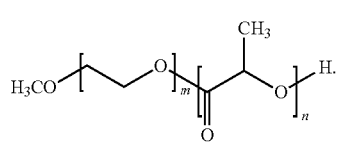

wherein m is between 1 and 10,000, n is between 1 and 10,000, or an active derivation thereof.

At the center or core of the micelle structure provided herein is superparamagnetic iron oxide nanoparticle (SPION). In some embodiments, the SPION is hydrophobic. In some embodiments, the SPION core comprises a coating of oleic acid and oleylamine. The SPION can be prepared by any method known to those of skill in the art. In one embodiment, the SPION is prepared using iron, 1,2-dodecanediol, oleic acid, oleylamine, and benzyl ether.

The compositions provided herein comprise a micelle having a superparamagnetic iron oxide nanoparticle (SPION) core, a first coating comprising one or more cationic polymers, and a second coating comprising a polynucleotide. In some embodiments, these compositions further comprise a ligand. A ligand is defined herein as any moiety that facilitates binding of the compositions provided herein to a target such as a cell. Ligands include, but are not limited to, antibodies, adhesion molecules, lectins, integrins, and selectins. When the ligand is an antibody, it can comprise approximately 1% of the total composition weight (but is not limited to such amount). In some embodiments, the ligand is an antibody specific for a cancer cell. In one embodiment, the antibody is specific for a prostate stem cell antigen.

The magnetic micelle compositions provided herein are useful for transfecting a cell with the polynucleotide bound to the composition. The Examples below describe that these magnetic micelle compositions provide for transfection rates and efficiencies higher than lipofectamine or PEI. Accordingly, provided herein is a method of transfecting a cell with a polynucleotide comprising, contacting the cell with a composition comprising a micelle having a superparmagnetic iron oxide nanoparticle (SPION) core, a first coating comprising a cationic polymer, and a second coating comprising a polynucleotide. Also provided herein is a method of transforming a cell with a polynucleotide comprising, contacting the cell with a composition comprising a micelle having a superparmagnetic iron oxide nanoparticle (SPION) core, a first coating comprising a cationic polymer, and a second coating comprising a polynucleotide. The compositions used in these methods can be any of those described above and below.

Also provided herein is a method of detecting transfection of a cell with a polynucleotide comprising, contacting the cell with a composition comprising a micelle having a superparmagnetic iron oxide nanoparticle (SPION) core, a first coating comprising a cationic polymer, and a second coating comprising a polynucleotide, using magnetic resonance imaging to detect a location of the SPION bound to the polynucleotide.

The methods provided herein can be performed on a cell ex vivo or in vivo. When performed in vivo, the compositions can be administered in any manner to a subject comprising the cell. In some embodiments, the compositions are administered intravenously. In other embodiments, the compositions are administered intraperitoneally. The methods can also comprise placing a magnet proximal to the cell prior to or during transfection or transformation.

These methods allow for the transfection and/or transformation of cancer cells including, but not limited to, prostate cancer cells. The examples below provide specific examples of compositions and methods used to transfect cells expressing a prostate stem cell antigen in vivo (See Example 10). These examples further describe the use of these compositions to visualize such transfection using magnetic resonance imaging.

It should be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. All patents, patent applications, and publications referenced herein are incorporated by reference in their entirety for all purposes.

EXAMPLES

Example 1

Preparation of Multilayered Mag-Micelles

Materials

Monomethoxy PEG (mPEG, Mw 2 kDa), branched PEI (Mw, 25 kDa), 3,6-dimethyl-1,4-dioxane-2,5-diose (DL-dilactide), Stannous 2-ethylhexanoate, 1,2-dodecanediol, oleylamine and cyanoborohydride were purchased from Sigma. Iron (III) acetylacetonate (Fe(acac)$_3$), oleic acid, and benzyl ether were purchased from Acros Organics. Water soluble chitosan (Mw, 10 kDa) was donated from Transgenex Nanobiotech Inc.

Synthesis of mPEG-Poly (D, L-Lactide) (PLA)-OH

A series of mPEG-PLA-OH diblock copolymers were synthesized from DL-dilactide and mPEG of various molecular weights using stannous 2-ethyl-hexanoate as a catalyst by catalyzed ring opening polymerization [A. Lucke, et al., Biomaterials 2000, 21, 2361]. First, the DL-dilactide was dried with vacuum at room temperature for 4 hours. The appropriate amount of mPEG was dried in a two-neck pre-dried round bottom flask with vacuum at 80° C. for 3 hours. Then certain amount of dry pure DL-dilactide, the stannous 2-ethyl-hexanoate (3% w/w) and 20 mL of toluene were added to two-neck flask and mixed with mPEG. The reaction solution was refluxed for 5 hours in an oil bath (140° C.) with argon gas protection. The product was precipitated with cold diethyl ether. The purified product was kept in vacuum at room temperature for 24 hours. To determine the structure of the synthesized copolymers, FTIR spectra were performed using a NEXUS spectrometer. The block ratio and the chemical structure of mPEG-PLA were characterized by 1H-NMR. The mPEG-PLA block copolymer was dissolved in CDCl3 and 1H-NMR spectrum was taken using a Bruker 250 spectrometer (Bruker, Rheinstetten, Germany).

Preparation of CS-Mag-Micelle

SPIONs were prepared according to the procedure reported by Sun, et al [S. H. Sun, and H. Zeng, Journal of the American Chemical Society 2002, 124, 8204.]. The black SPION product was dissolved in dichloromethane in the presence of oleic acid (0.05 ml) and oleylamine (0.05 ml). The solvent evaporation method was used to prepare CS-mag-micelle by adding an SPION/mPEG-PLA dichloromethane solution dropwise to a chitosan solution with vigorous stirring. In a typical experiment, the mixture of 500 μl of 25 μg/μl mPEG-PLA in $CH_2Cl_2$ and 300 μl of 4 mg/ml SPION in $CH_2Cl_2$ solution was added drop wise to 10 ml of a 10 mg/ml solution of water-soluble chitosan with stirring. The organic solvent $CH_2Cl_2$ was allowed to evaporate slowly at ambient conditions overnight. The micelle solution was filtered through a nylon membrane filter (size cutoff 0.2 um) and freeze-dried.

To prepare different weight ratios of chitosan-PEI-mag-micelles (also referred to as 4M-NPs) (chitosan to PEI weight (wt) ratios, 7:3, 5:5, 3:7), different volumes of CS-mag-micelle solutions (2 mg/ml) were mixed with a PEI solution (2 mg/ml). X-ray diffraction (XRD) measurements were acquired using a Rigaku D/Max diffractometer equipped with Cu—Ku radiation, λ=0.154185 nm. The magnetic data were taken with a vibrating sample magnetometer (Model 4500 by EG&G/Princeton Applied Research Corp) at room temperature.

Plasmid Preparation

The plasmid pCMV-tdTomato (Clontech) encoding the tdTomato red-fluorescent protein was grown in XL1-Blue cells and purified by MaxiPrep plasmid purification kit (Invitrogen Corporation, Carlsbad, Calif.). The pRL *renilla* luciferase plasmid (Promega Corporation, Madison, Ill.) and pSV40 luciferase were grown in *E. coli* XL10. The DNA concentration and purity were determined prior to using in transfection assays.

Preparation of 4M-NP:DNA Complexes

The 4M-NPs (0.2 μg/μl, 10 kD) and a plasmid DNA solution (0.2 μg/μl) in PBS were prepared separately. The plasmid DNA solution was added dropwise to CP-mag-micelles solution and vortexed for 20 minutes.

Example 2

Characterization of Multilayered Mag-Micelles

The assembly of a magnetic micelle is shown in FIG. 1. The hydrophobic SPIONs were synthesized according to the procedures of Sun et al [S. H. Sun, and H. Zeng, Journal of the American Chemical Society 2002, 124, 8204.]. The XRD spectra confirmed the formation of Fe3O4 (FIG. 2A) [C. W. Jung, and P. Jacobs, Magnetic Resonance Imaging 1995, 13, 661; 37]. The particle size determined from the Scherrer Broadening of the XRD lines is 7.0±0.6 nm. (All data provided herein are expressed as mean plus or minus standard deviation. Statistical analysis was performed using the unpaired Student's t-test. Differences were considered statistically significant for $p<0.05$.) TEM images (FIG. 2C) showed an average size of 6 nm in agreement with the XRD results. The magnetic properties of the SPION powder at 300K analyzed using a vibrating sample magnetometer show no hysteresis (FIG. 2B) characteristic of superparamagnetism with saturation magnetism Ms equal to approximately 23 emu/g. This magnitude of Ms is consistent with that reported for similarly prepared 6 nm $Fe_3O_4$ NPs with a blocking temperature of about 20K [P. Dutta, et al., Journal of Applied Physics 2009, 105].

Figure 2:
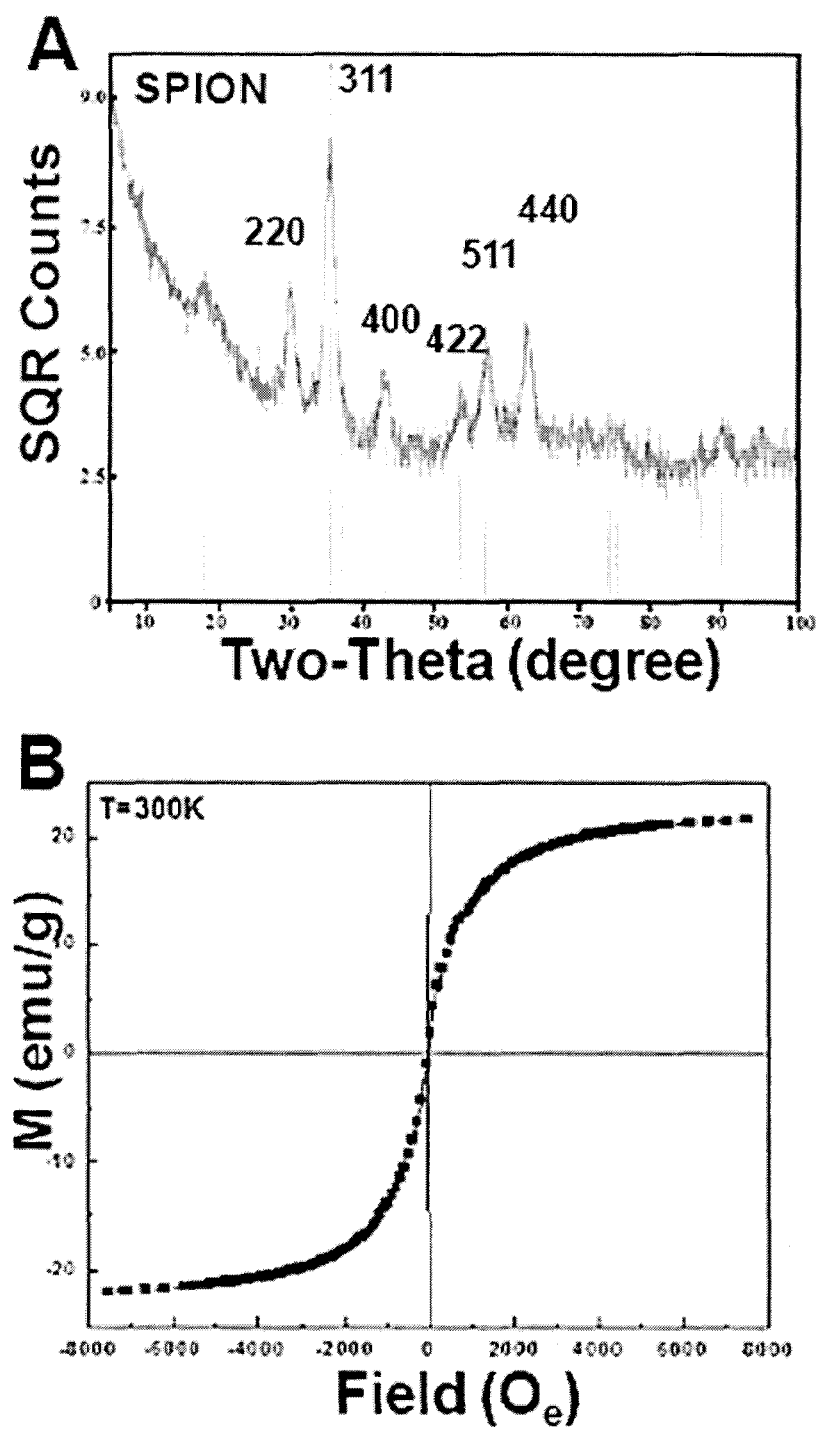
FIG. 2 shows XRD spectra of SPION (A), magnetization vs. magnetic field of SPIONs 300K (B), TEM of SPIONs (C), mag-micelle (D), 4M-NPs (chitosan:PEI wt ratio, 5:5) (E), and 4M-NPs:DNA (chitosan:PEI:DNA wt ratio, 5:5:1 (F).
Figure 2:
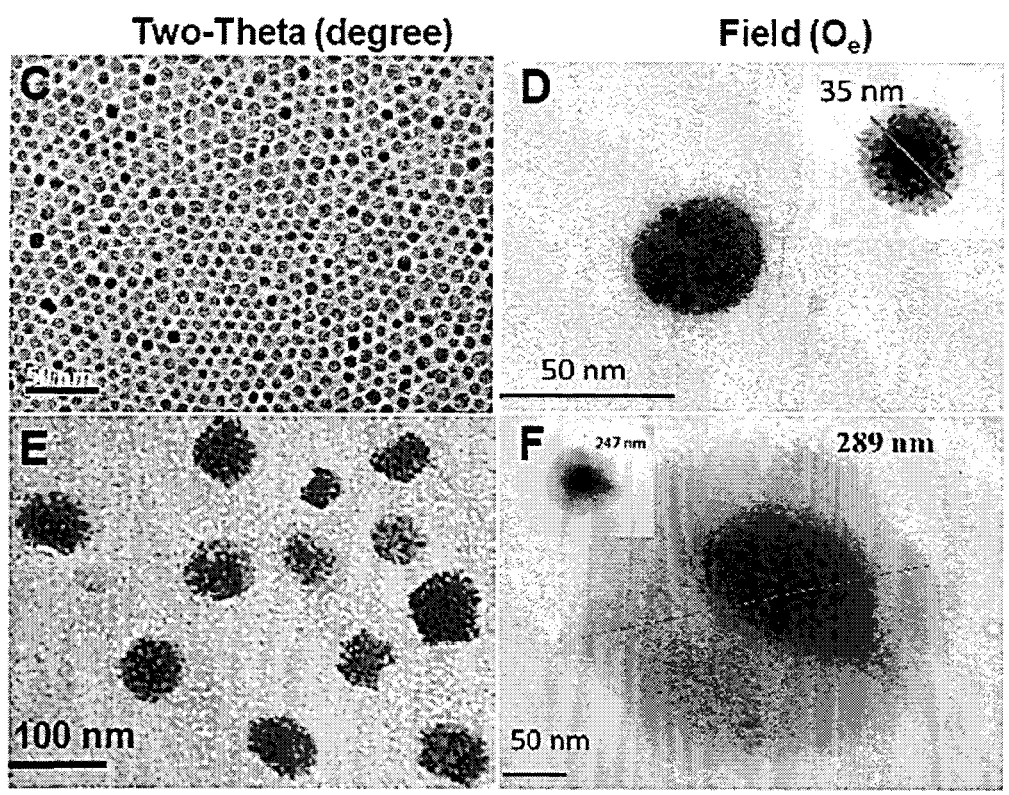
Figure 3:
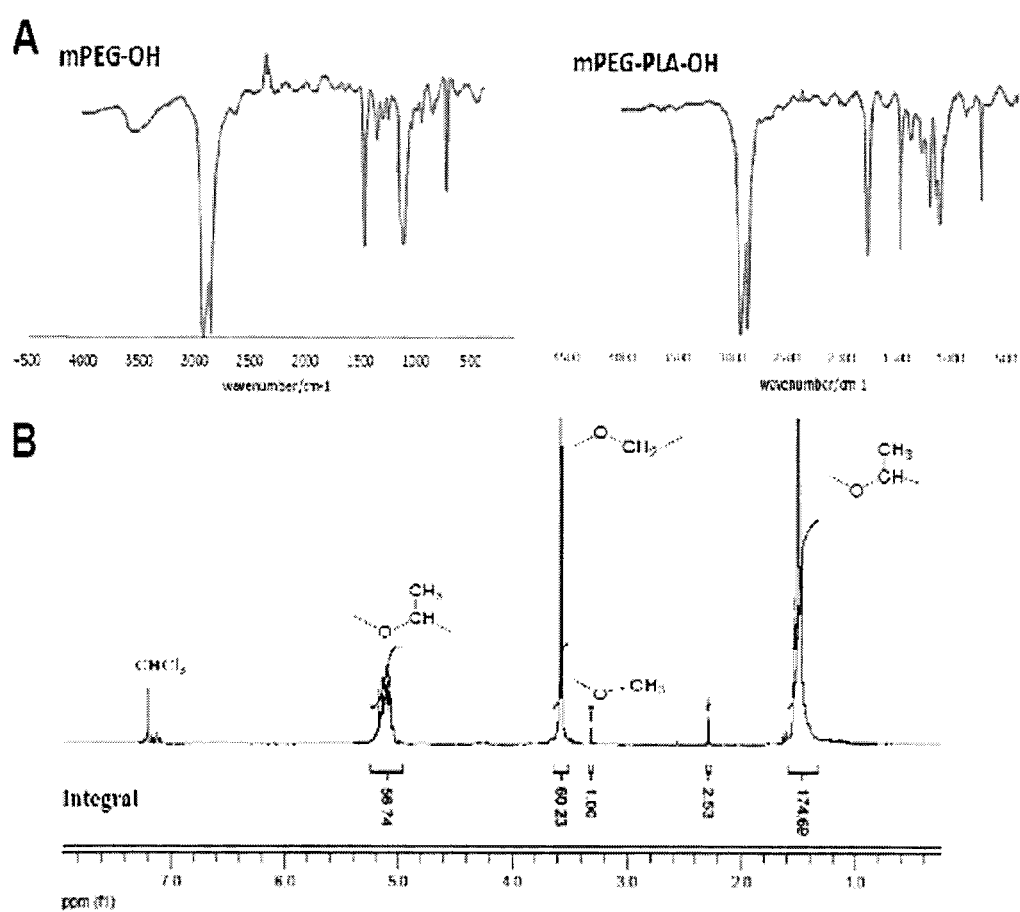
FIG. 3 shows FTIR spectrum of mPEG-OH and mPEG-PLA-OH (A) and NMR of mPEG-PLA (B).
Figure 19:
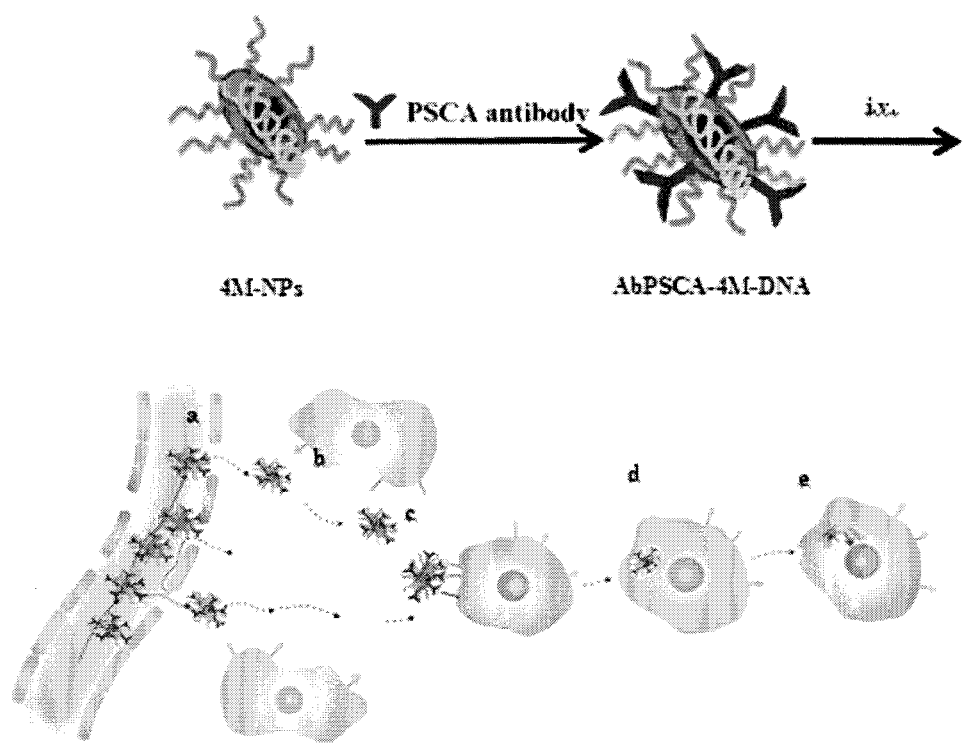
FIG. 19 shows a schematic illustration of the PSCApAb-4M-DNA synthesis and targeting gene delivery to the cancer cells. NPs extravasate from leaky tumor vessels (a&b), diffuse past non-target cells lacking antigens for the targeting peptide (c) bind to antigen on target cancer cells (d), internalize to the cells (e) and release DNA to nucleus.

SPIONs were coated with hydrophobic chains from oleic acid and oleylamine that are self-assembled as needle shape, as shown in FIG. 19. To increase sensitivity of MRI, hydrophobic SPIONs were loaded into the core of micelles (referred to as mag-micelles) self-assembled from an amphiphilic block copolymer of mPEG-poly (D, L-lactide) (PLA). The block copolymer mPEG-PLA was synthesized by a ring opening polymerization of D, L-lactic acid using monomethoxy-terminated PEG (2KD) as a macro-initiator and Sn(Oct)2 as catalyst. The block copolymer was characterized by FTIR and NMR. FIG. 3A shows the FTIR of mPEG and mPEG-PLA. The strong absorption at 1760 cm−1 is assigned to —C=O stretch of PLA, while the band at 1087 and 1184 cm−1 is due to C—O—C stretch of PEG and PLA, respectively. The 1HNMR was obtained to further confirm that PLA was copolymerized with mPEG as shown in FIG. 3B. The integrity of the signal at 3.3 ppm, which is attributed to the three equivalent hydrogen atoms of the methyl group on mPEG-OH was used as the internal standard. The molecular weight of the PLA block in the copolymer was calculated to be 13 kDa using an internal standard. The diameter of mag-micelles spheres ranged from 35 to 50 nm, as shown in FIG. 2D.

Figure 4:
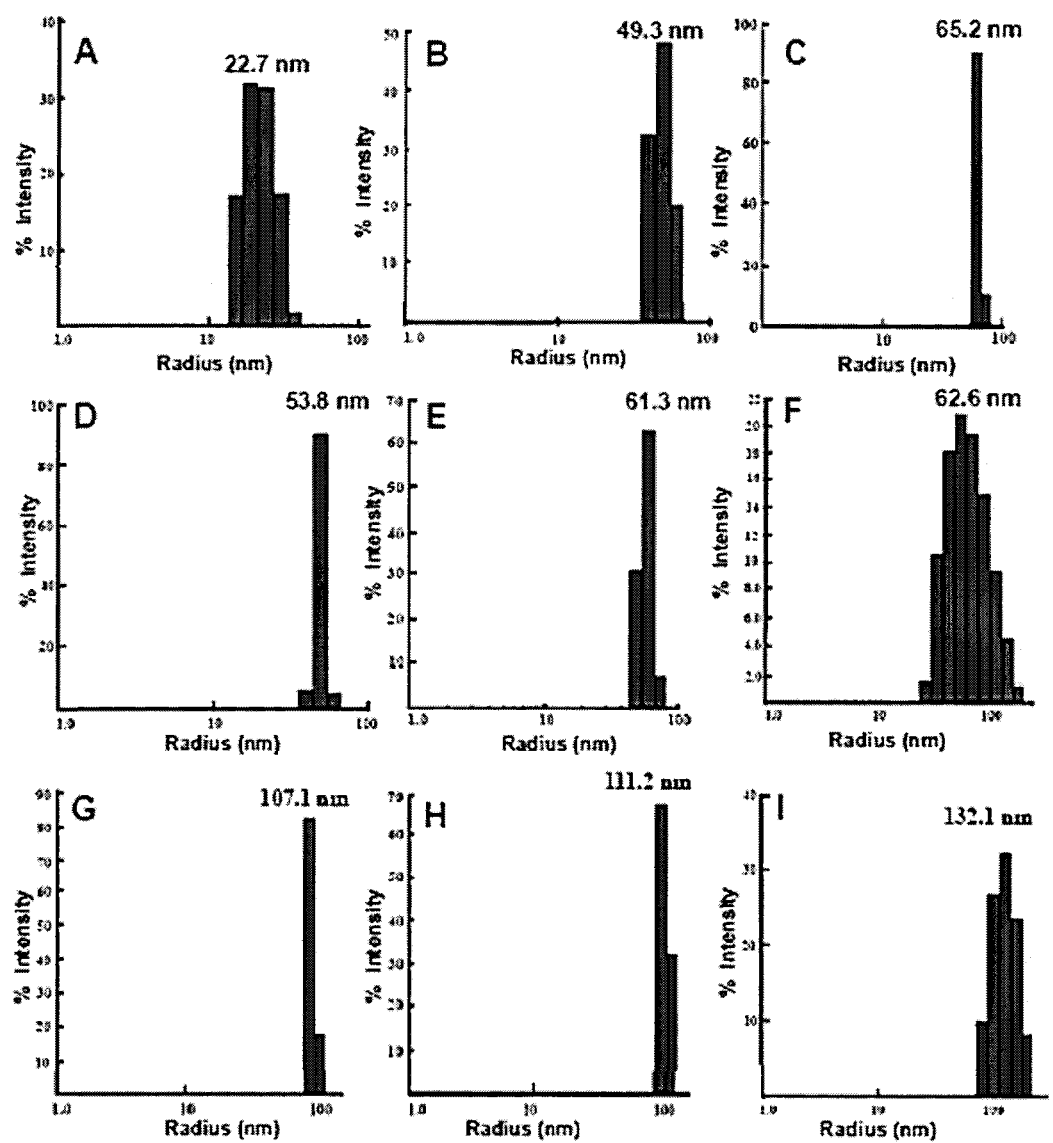
FIG. 4 provides a DLS that shows the size distribution of mag-micelles (A), CS-mag-micelles (B), 4M-NPs (wt ratio, 7:3) (C), 4M-NPs (chitosan:PEI wt ratio, 5:5) (D), 4M-NPs (chitosan:PEI wt ratio, 3:7) (E), CS-mag-micelles:DNA (chitosan:DNA wt ratio, 10:1) (F), 4M-NPs:DNA (chitosan:PEI:DNA wt ratio, 7:3:1) (G), 4M-NPs:DNA (chitosan:PEI:DNA wt ratio, 5:5:1) (H), and 4M-NPs:DNA (chitosan:PEI:DNA wt ratio, 3:7:1) (I).

To ensure biocompatibility and stability in vivo and proper intracellular trafficking, the magmicelles were coated with the cationic polymers, chitosan and PEI. First, the chitosan coated mag-micelles (CS-mag-micelles) were prepared by solvent evaporation. Second, PEI was added to CS-mag-micelles at different weight (wt) ratios to form chitosan-PEI coated mag-micelles (4MNPs). A 50 kDa molecular weight cutoff dialysis bag was used to remove uncoated PEI, and DLS was used to measure the distribution of the size and the peak of the hydrodynamic diameter of different layers of mag-micelles in aqueous solutions (FIG. 4). In particular, the hydrodynamic particle sizes of the mag-micelles, 4M-NPs and 4M-NPs:DNA complex in DMEM cell culture media were measured at 25° C. using a DynaPro DLS plate reader (Wyatt Technology. Germany). The morphology of the SPIONs and multi-layered mag-micelles was determined by TEM.

The average hydrodynamic diameter of CS-mag-micelle is 49.8 nm (FIG. 4B), which is bigger than the diameter of mag-micelle (22.7 nm). When PEI was added to the coating of CS-mag-micelle, the average diameters of 4M-NPs were further increased. 4M-NPs with different wt ratios of chitosan:PEI, 7:3, 5:5 and 3:7, formed the average diameters of 65.2 nm, 53.8 nm, and 61.3 nm, respectively. The morphology of mag-micelles and 4M-NPs was determined by TEM. FIGS. 3D and 3E show well-defined core/shell structures of mag-micelles with a high density of SPION clusters inside the micelles. The size (diameter) of the 4M-NPs was 50-70 nm, which is somewhat larger than the mag-micelles (35-40 nm).

The tomato-DNA plasmids were bound to the surface of 4M-NPs by electrostatic forces. As shown in the TEM images (FIG. 3F), the surface of the 4M-NPs was encircled by DNA plasmids. The size distribution of the 4M-NP:DNA complex is shown in FIG. 4. The average hydrodynamic diameter of the 4M-NP:DNA complex increased with PEI concentration on the coatings from 107.1 nm with chitosan:PEI:DNA at a wt ratio of 7:3:1 to 132.1 nm with a chitosan:PEI:DNA wt ratio of 3:7:1.

Figure 5:
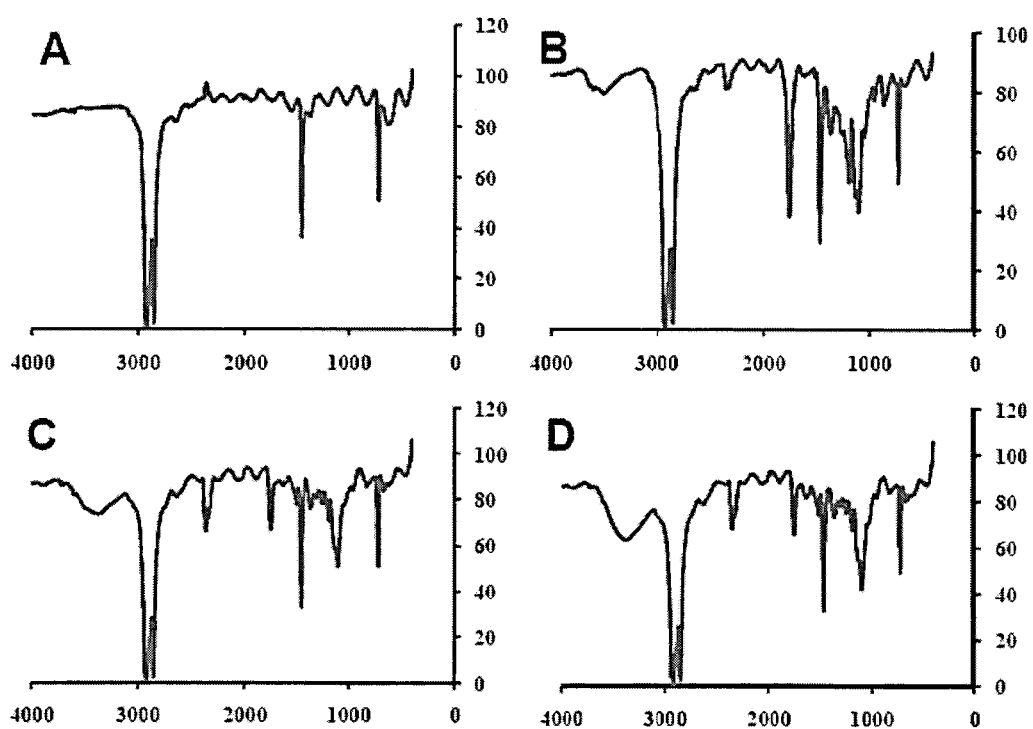
FIG. 5 shows FTIR spectrum of SPIONs (A), mag-micelles (B), CS-mag-micelles (C), and 4M-NPs (chitosan:PEI wt ratio, 5:5) (D).

The formation of the multilayered mag-micelles was further confirmed by FTIR. FIG. 5A shows the FTIR bands characteristic of oleic acid-coated hydrophobic SPION. The bands at 574 and 424 cm−1 were due to Fe—O vibration bands. Surface bonded oleic acid can be observed by the presence of 2911 and 2846 cm−1 assigned to C—H stretch, and 1461 cm−1 (C—H bending). In the FTIR of mag-micelle (FIG. 5B), absorption peaks due to mPEG-PLA (e.g., 1037 and 1139 cm−1 peaks from PEG C—O—C and PLA, and 1749 cm−1 peak from C=O stretching bands respectively) were observed. In addition, 3200-3600 cm−1 broad band from O—H stretching was also observed. In the FTIR of CS-mag-micelle (FIG. 5C) and 4M-NP (FIG. 5D) more broad bands at 3200-3600 cm−1 due to N—H and O—H stretching were observed.

Example 3

Complexes of 4M-NPs and DNA

Figure 6:
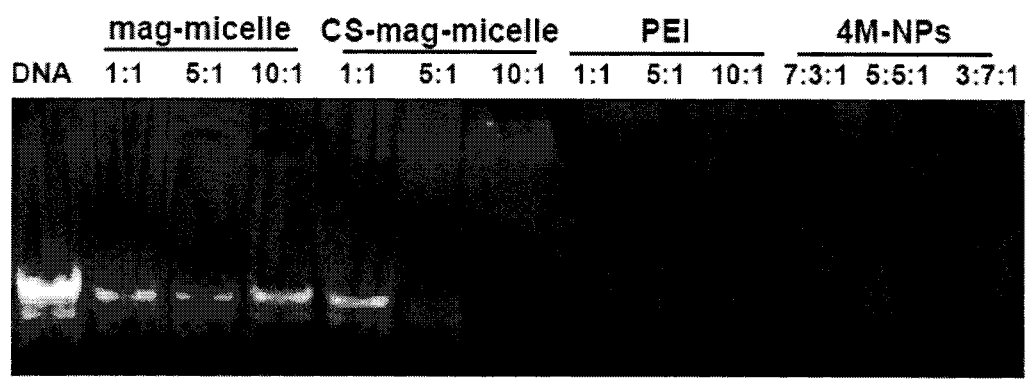
FIG. 6 shows gel electrophoresis of the complexes of mag-micelles, CS-mag-micelles, PEI and 4M-NPs with DNA at different weight ratios.

The ability of the vector to form complexes with polynucleotides is a fundamental requirement for gene delivery. The condensation capability of different layers of mag-micelles with DNA was evaluated using agarose gel electrophoresis as shown in FIG. 6. In this assay, the 4M-NPs:DNA complexes were mixed with a loading buffer and loaded onto a 0.8% agarose gel containing ethidium bromide. Gels were electrophoresed at room temperature in Tris/Borate/EDTA buffer at 80 V for 60 min. DNA bands were visualized using a Chemi DOX TM XRS imaging system (Bio-RAD, CA, USA). DNA which was bound to the mag-micelles remained in the loading wells, while unbound DNA migrated down the agarose gel.

It was observed that CS-mag-micelles could not completely retarded DNA until the chitosan:DNA wt ratio reached 10:1. However, the migration of DNA was retarded completely with 4M-NPs irrespective of chitosan:PEI wt ratios. These results suggest that PEI enhanced DNA binding to mag-micelles. During transfection it is critical to protect DNA from degradation by nucleases and destructive enzymes within lysosomes, which can reduce transfection efficiencies. We examined whether the addition of PEI to CS-mag-micelles could improve binding capacity and protection of DNA. The gel retardation analysis provided information about DNA protection by the mag-micelles. FIG. 6 shows that DNA bound by CSmag-micelle at a wt ratio of 5:1 or 10:1 was not protected as evidenced by ethidium bromide staining in the loading wells. On the other hand, PEI and 4M-NP fully protected bound DNA from staining, as seen by a lack of visualized DNA in the wells.

Example 4

Cell Transfection Assay

The ability of 4M-NPs to deliver plasmid DNA to various cultured cells in vitro was tested using plasmid DNA encoding tomato protein (pCMVtdTomato) as a reporter (with excitation and emission maxima equal to 554 and 581 nm, respectively). To visualize the gene delivery efficacy, cells were plated in 96-well plates overnight and then incubated with various transfection agents 2 µg/ml DNA. A magnet was placed under the plate for half hour to enhance the transfection. The magnet was removed and the cells were incubated for 48 hours.

Figure 7:
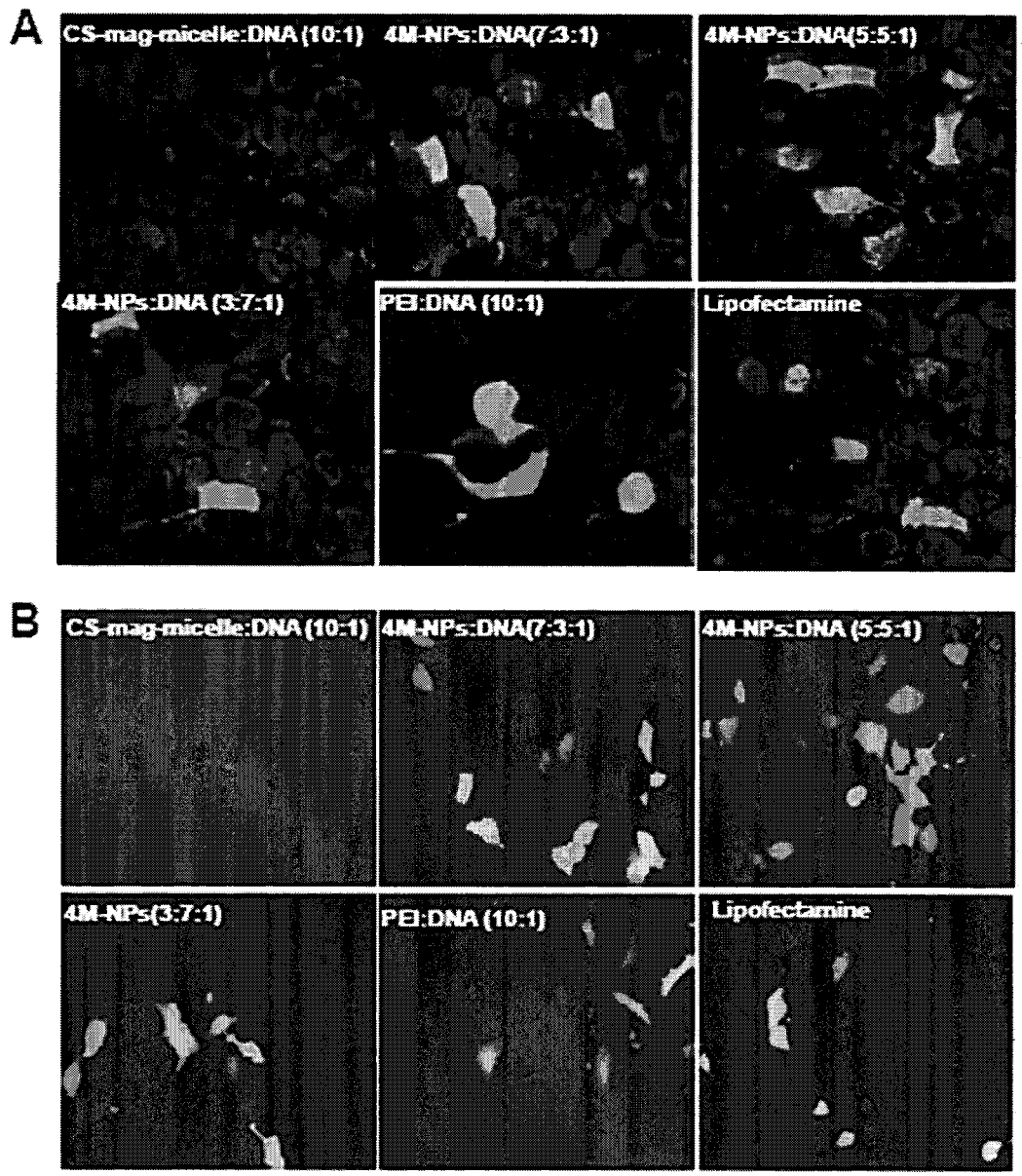
FIG. 7 shows cells that were transfected with indicated NPs complexed with tomato red-fluorescent protein plasmid. Forty-eight hours after transfection, tomato protein expression was examined. Confocal microscopic images (200×) of HEK293. Nuclei were stained with DAPI (A). Fluorescence images (40×) of 3T3 cells (B). 4M-NPs:DNA with different chitosan:PEI:DNA wt ratios.
Figure 20:
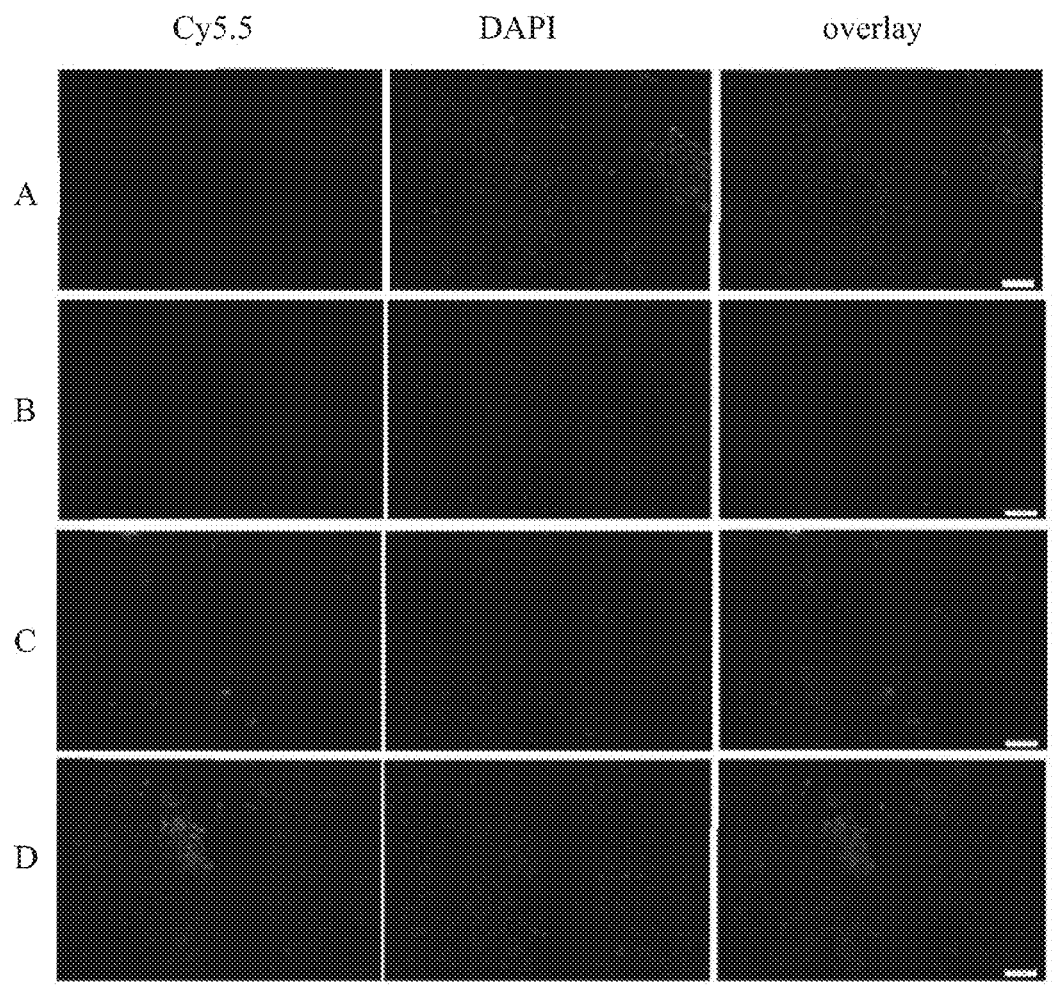
FIG. 20 shows confocol microscope images corresponding to the binding affinity of the Cy5.5-labeled PSCA-4M-NPs to TRAMP cells. (A) Cy5.5-4M-NPs, (B) Cy5.5-PSCA-4M-NPs (0.25 wt % PSCA), (C) Cy5.5-PSCA-4M-NPs (0.5 wt % PSCA), (D) Cy5.5-PSCA-4M-NPs (1.0 wt %)

The fluorescent images in FIG. 7 (A, B) show that nanocomplexes of PEI:DNA (wt ratio, 10:1) and chitosan-PEI coated mag-micelles (4M-NPs) irrespective of chitosan:PEI wt ratios, readily delivered tomato DNA in HEK293 and 3T3 cells. Consistent with gel retardation data, chitosan-DNA nanocomplexes, even at higher wt ratios (chitosan:DNA, 10:1) did not transfect cells. Similar results were obtained when PC3 cells were transfected with various 4M-NPs (FIG. 20). Cells receiving no treatment were also imaged for reference. These results demonstrate the ability of 4M-NPs to deliver DNA into the cells and produce expression levels similar to those commercially available transfection agents, such as lipofectamine.

Transfection efficiency was quantified using *Renilla* luciferase reporter plasmids (pRE-luc). HEK293 cells were transfected with nanocomplexes consisting of various combinations of 4MNPs and pRE-luc. In particular, the cells were plated in 12-well plate at a density of 105 cells per well in 1 ml of complete medium. After 48 hours incubation with plasmid (tomatoDNA:pRLLuciferase:SUV40-luciferase (wt ratio, 10:1:1)) complexed nanovectors, cells were collected with 50 µl of 1× cell-passive buffer (Promega). The luciferase activity in cell extracts was measured using a dual luciferase assay kit (Promega) on a luminometer. The light units (LU) were normalized against protein concentration in the cell extracts, which was measured using a BCA protein assay kit (ThermoScientific). Luciferase activity in cell lysates was expressed as relative light units (LU/min per µg of protein in the cell lysate).

Figure 8:
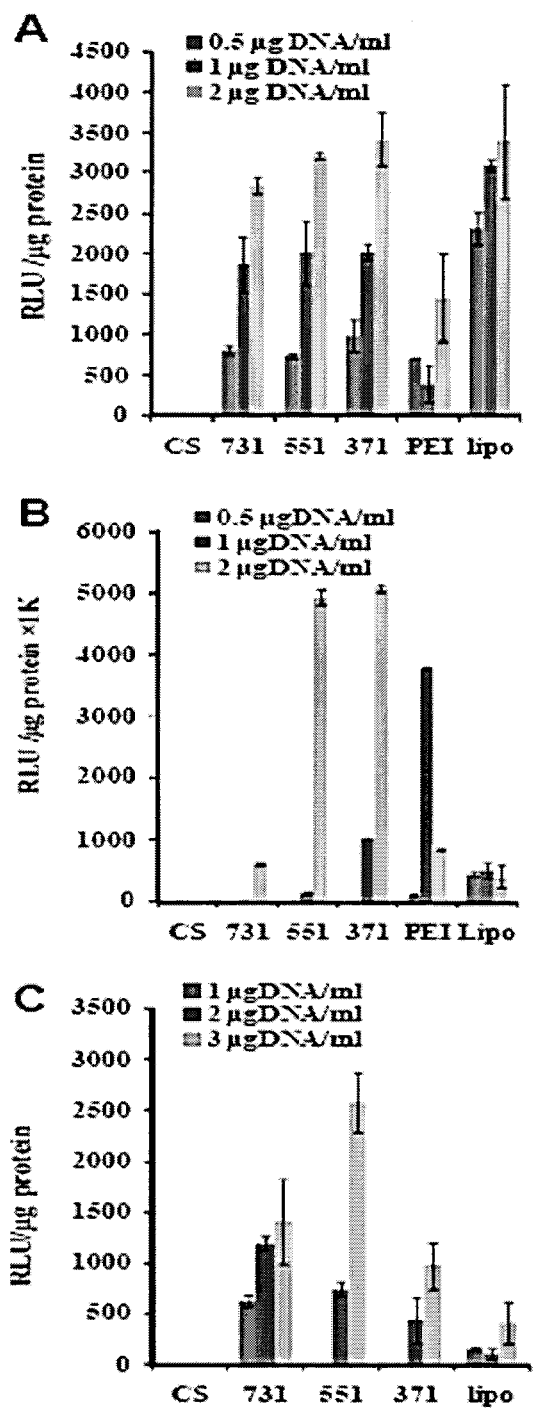
FIG. 8 shows transfection efficiencies of HEK 293 cells (A), 3T3 cells (B), and PC3 cells (C) treated with either CS-mag-micelles:DNA (10:1) (CS), 4M-NPs:DNA complexes with varying wt ratios, chitosan:PEI:DNA (7:3:1), chitosan:PEI:DNA (5:5:1), chitosan:PEI:DNA (3:7:1), PEI:DNA (10:1) (PEI), and Lipofectamine (lipo).

Results shown in FIG. 8A suggest that in HEK 293 cells, nanocomplexes of 4M-NP with DNA induce luciferase activity similar to lipofectamine-DNA complex, and higher than with PEI-DNA complexes. The transfection efficiency of 4M-NPs as a function of DNA dose was also evaluated. At 0.5 µg DNA/ml, the transfection efficiency of all three 4M-NP:DNA complexes, with chitosan:PEI:DNA wt ratios, 7:3:1, 5:5:1 or 3:7:1 is comparable to that of PEIDNA complexes. When the dose of DNA was further increased from 1 to 2 µg DNA/ml, the transfection efficiencies of 4M-NPs were much higher than PEI and were comparable to lipofectamine.

The potential of 4M-NPs to deliver DNA to 3T3 cells was also examined, since these cells are resistant to transfection with chitosan-DNA particles [T. Dastan, and K. Turan, Journal of Pharmacy and Pharmaceutical Sciences 2004, 7, 205]. At low DNA concentrations (0.5 µg DNA/ml), the transfection efficiency of 4M-NP and PEI for 3T3 cells was lower than with Lipofectamine (FIG. 8B). When the DNA concentration was increased to 1 µg/ml, the transfection efficiency of 4M-NP increased with an increase in PEI wt ratio. The transfection efficiency of 4MNP: DNA (with chitosan:PEI:DNA wt ratio, 3:7:1) was higher than lipofectamine, but significantly lower than PEI:DNA (10:1). However, at 2 µg DNA/ml, the cell transfection efficiency of all three 4M-NPs increased significantly compared to Lipofectamine. The transfection efficiency of 4M-NP:DNA (5:5:1 and 7:3:1) was 10-fold more than Lipofectamine and PEI:DNA (10:1). These results demonstrate that nanocomplexes of 4M-NPs can transfect 3T3 cells with high efficiency compared to Lipofectamine or PEI.

The transfection efficiency of 4M-NPs in the difficult-to-transfect cancer cell line, PC3, was next determined. As shown in FIG. 8C, the transfection efficiency 4M-NPs in PC3 cells depended on the dose of DNA irrespective of the PEI wt ratio. At 1 or 2 µg DNA/ml, 4M-NP:DNA (with chitosan:PEI:DNA wt ratio, 7:3:1) showed the highest cell transfection efficiency, which was significantly higher than lipofectamine. The highest transfection efficiency was seen with 4MNP:DNA (chitosan:PEI:DNA wt ratio, 5:5:1) complexed with 3 µg/ml DNA.

From these results it can be concluded that the synergistic effect of chitosan and PEI endowed 4M-NP with the ability to produce a greater transfection efficiency than PEI itself and one that is comparable or better than lipofectamine depending on the dose and cell lines. The degree of synergistic effect of chitosan and PEI depends on the structure of the nanoparticles and the type of cell line, as reported [H. L. Jiang, et al. Journal of Controlled Release 2008, 131, 150]. The ability of chitosan/PEI to transfect cells better than chitosan alone can be attributed to the higher amine content in the complex and the PEI's proton sponge effect that facilitates the escape of DNA from endosomes. The transfection efficiency of chitosan/PEI is higher than that of PEI alone due in part to the weaker condensation ability of the complex, which would result in an easier release of DNA from the complexes inside the cells [K. Wong, et al. Leong, Bioconjugate Chemistry 2006, 17, 152].

Example 5

Cell Toxicity Test

To investigate the cytotoxicity of 4M-NPs, cell viability was determined by WST assay. In particular, in vitro cytotoxicity was evaluated in PC3 cells using the WST-1 colorimetric assay with 2-(4-iodophenyl)-3-(4-nitrophenyl)-5-(2,4-disulfophenyl)-2H-tetrazolium monosodium salt reagent. PC3 cells were seeded in a 96-well plate using standard DMEM supplemented with 10% fetal bovine serum and 1% penicillin G and streptomycin. Various concentrations of nanoparticles were added to the well in triplicate. The cells were cultured for 72 hours in an incubator at 37° C. under 5% CO2. After 68 hours, 10 µL of WST-1 (diluted 1:4 with phosphate buffer) was added and cells were incubated for an additional 4 hours. Cell viability was measured at 450 nm in a microplate reader (Synergy H4 Hybrid reader, Biotek). Cell viability (%) was calculated according to the following equation:

Cell Viability (%)=OD Sample/OD Control×100

Figure 9:
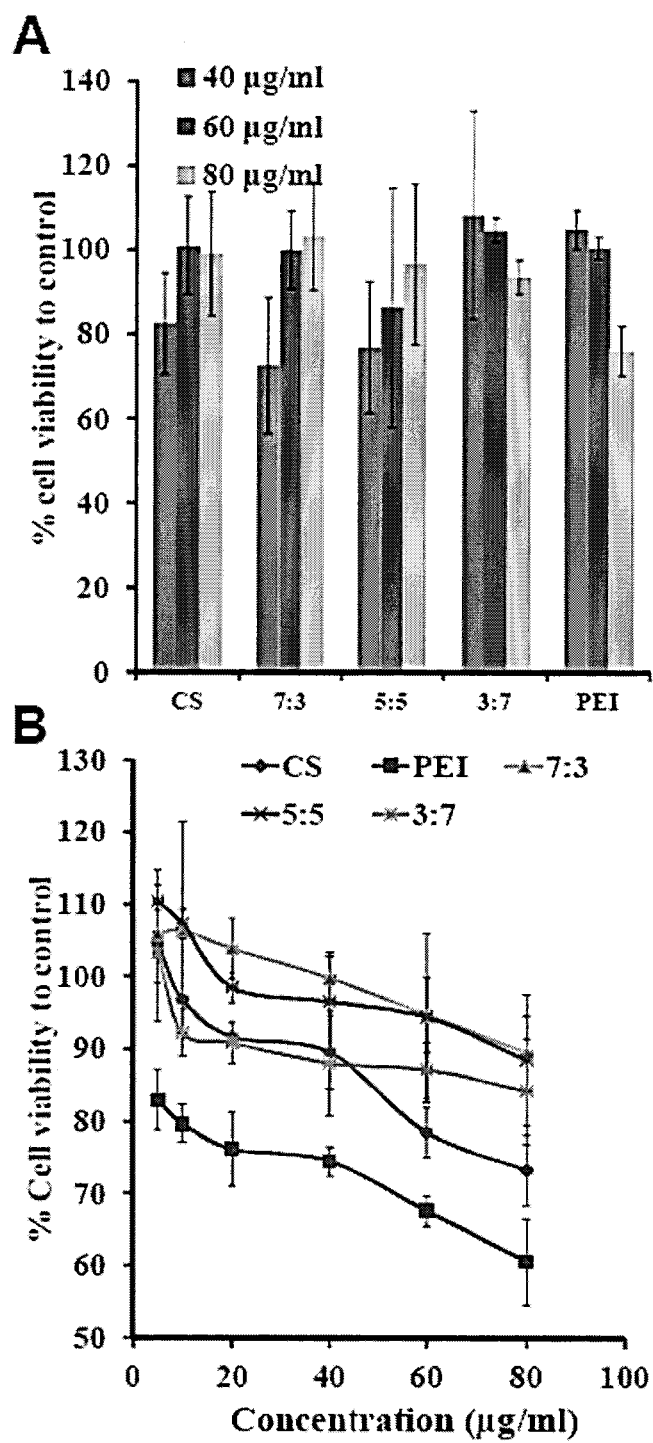
FIG. 9 shows the viability of PC3 (A) and HEK293 (B) cells treated with different concentrations of CS-mag-micelle, 4M-NPs (7:3), 4M-NPs (5:5), 4M-NPs (3:7) and PEI.

The results in FIG. 9 show that CS-mag-micelles and 4M-NPs had lower cytotoxicity than PEI. The 4MNPs with chitosan:PEI wt ratios of 7:3 and 5:5 did not show any cytotoxicity even at the high concentration of 80 µg/ml in PC3 cells. However, 4M-NPs with chitosan:PEI at a wt ratio, 3:7 showed a dose-dependent increase in cytotoxicity. These results indicated that 4M-NPs with chitosan:PEI wt ratios of 7:3 and 5:5 are ideal for delivering genes with no toxicity. The later was chosen for in vivo studies.

Example 6

Cell Uptake Mechanism

Nanoparticles can be internalized either by receptor mediated endocytosis or by macropincytosis, caveolae-mediated endocytosis and lipid raft-mediated endocytosis on cell membranes via hydrophobic or electrostatic interactions [L. Y. T. Chou, et al., Chemical Society Reviews 2011, 40, 233]. In order to determine the mechanism of cellular uptake and intracellular distribution of 4M-NPs, PC3 cells were transfected with the 4M-NPs for 24 hours, then trypsinized, fixed and analysed by TEM.

More specifically, cells were seeded 24 hours prior to transfection into a 96-well plate at a density of 5000 cells per well in 100 µl of complete medium (DMEM containing 10% FBS, supplemented with 2 mM glutamate, 50 U/ml penicillin and 50 µg/ml streptomycin). At the time of transfection, the medium in each well was replaced with 500 µl of fresh complete medium. An amount of nanoparticles equivalent to 0.2 µg of DNA was added to each well. The plate was placed on a magnet for 30 minutes and then incubated for 48 hours. Transfection with lipofectamine-DNA (Lipofectamine™, LTX, Invitrogen) complexes was performed as positive controls according to the manufacture's protocol. All transfection experiments were performed in triplicate.

Figure 10:
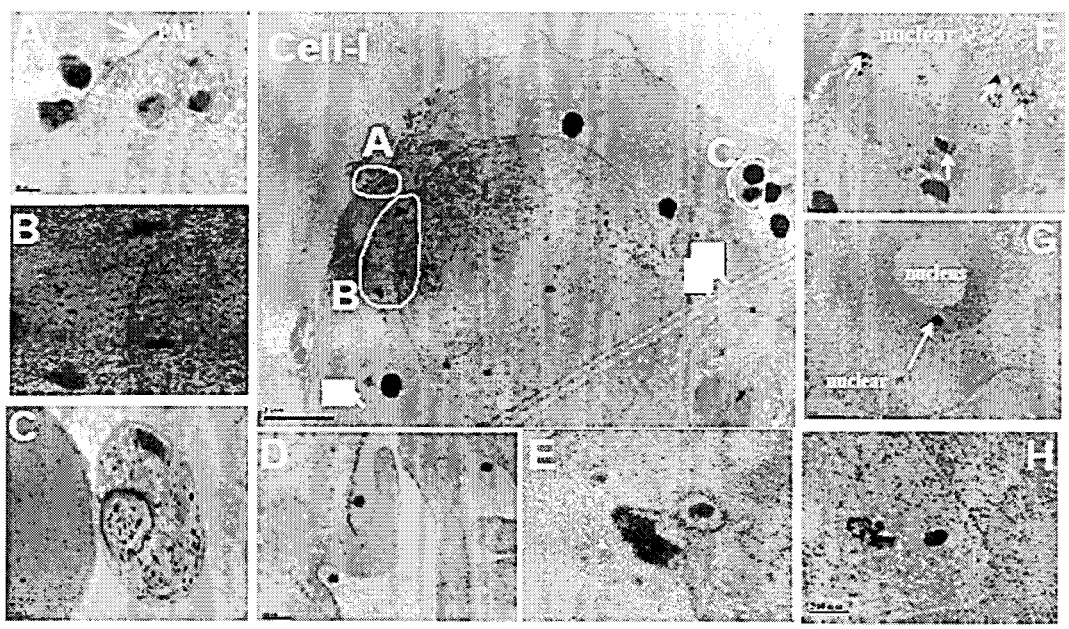
FIG. 10 shows TEM images showing uptake and intracellular distribution of 4M-NP:DNA (chitosan:PEI:DNA wt ratio, 5:5:1) by PC3 cells (A-C). Representative expanded images of Cell-I (D-H).

As shown in FIG. 10, NPs attached to the plasma membrane (FIG. 10A) were endocytosed by macropinocytosis (FIG. 10D) or lipid raft-mediated endocytosis (FIG. 10E). The NPs were present inside endosomes in the cytoplasm as shown in FIGS. 10A (3) and 10A (4).

After endocytosis, nanoparticles in endosomes can move into the cytoplasm by the aid of PEI [H. Duan, S, Nie, Abstracts of Papers of the American Chemical Society 2007, 233], which absorbs the protons produced during the acidification process in the mature endosome. In order to maintain electric neutrality, a parallel influx of Cl-1 ions and water accompanies the influx of protons. This process can induce swelling and eventual rupture of the endosomal membrane allowing its contents to escape.

Figure 21:
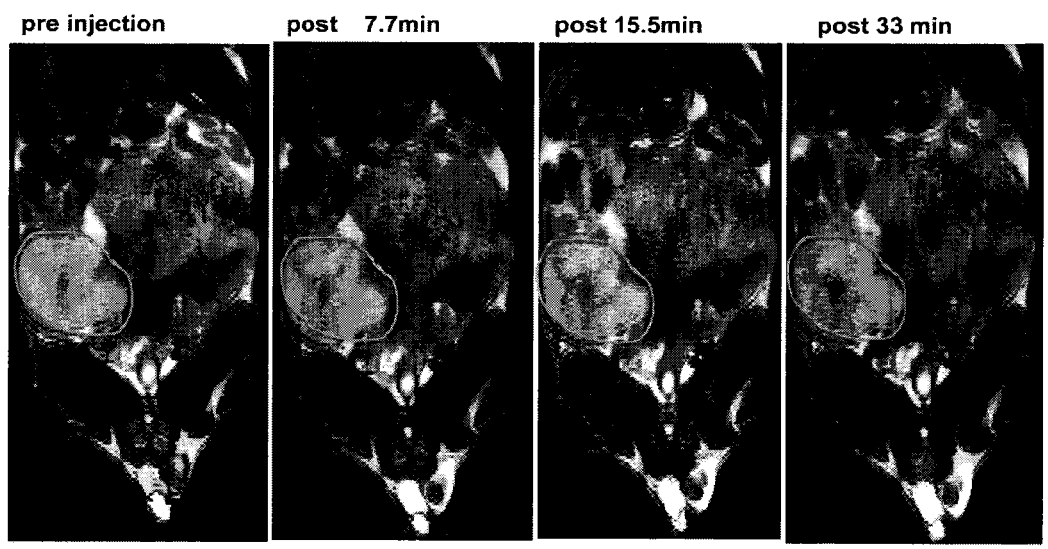
FIG. 21 shows in vivo T2 MR imaging of AbPSCA-4M-DNA distribution in TRAMP mice.

FIG. 10 H shows the rupture of the membrane of the endosome and escape of the 4M-NPs moving toward the nuclear membrane. Some particles pass through the nuclear membrane via nuclear pores and enter the nucleus as shown in FIG. 10 B, F, G. Further, some 4M-NPs were taken up by the liposome as shown in FIG. 10 C. Similar results were observed in HEK 293 cells as shown in FIG. 21.

To better visualize the escape of 4M-NPs from endosomes, the 4M-NPs were complexed with Cys5.5, a near-infrared imaging dye to track the 4M-NPs after transfection. HEK293 cells were transfected with Cy5.5 complexed with 4M-NP (chitosan:PEI wt ratio, 5:5) for 3 hours, nuclei were stained blue with the DNA-staining agent, DAPI, and the distribution of nanoparticles inside the HEK 293 cells was examined by confocal fluorescent microscopy.

More specifically, PC3 or HEK 293 cells were incubated with 4M-NP:DNA complex (5:5:1) for 24 hours. The cellswere trypsinized and immediately prefixed in 1% paraformaldehyde and 0.5% glutaraldehyde buffered with 0.5% sodium cacodylate (pH 7.1) for 10 min at 4° C., then pelleted by centrifugation at 1200 rpm for 5 minutes. The cell pellets were fixed in 2% paraformaldhyde-2.5% glutaraldehyde-0.05% sodium cacodylate, pH 7.1 for 30 minutes at 4° C.

After centrifugation, the pellets were collected and washed with 0.2 M sodium cacodylate, pH 7.4. Osmium tetroxide (1%) in sodium cacodylate buffer was then used for 1 hour for post-fixation at room temperature, followed by three washings in deionized water. Dehydration of cell pellets was then performed in an ascending series of ethanol concentrations—10%, 35%, 50%, 70%, 95% and 100% ethanol—for ten minutes each, followed by 100% acetone dehydration for 10 minutes. The pellets were then infiltrated with Embed 812 epoxy resin (Electron microscopy Science, Fort Washington, Pa.) in a stepwise manner with ratios of acetone to Embed of 3:1, 1:1, 1:3 for 30 min each.

Finally, the pellets were transferred into pure resin for 24 hours, and allowed to harden at 40° C. and 60° C. for 24 hours respectively. Ultrathin sections were cut with a Leica ultramicrotome and imaged with a JEOL 1200 EX transmission electron microscope, operating at an accelerating voltage of 80 kV. The cell uptake of 4M-NPs was also visualized with fluorescent labeled micelles, which were prepared by reacting Cys5.5-NHS with 4M-NP (wt ratio 5:5) overnight. The Cys 5.5-4M-NP was added to the HEK 293 cells, which were prelabeled with Green Cell Tracker (Invitrogen). Cells were viewed using an Olympus IX31 laser confocal microscope with spinning disk and live-cell pathology device. Three hours after Cys 5.5-4M-NP incubated with HEK293 cells, the cells were fixed and stained with DAPI. The distribution of nanoparticles inside the cells was imaged with the multiphoton Olympus BX61W1 confocal microscope.

Figure 11:
FIG. 11 shows laser confocal microscopic images (600×) of HEK293 cells incubated with Cys5-4M-NPs (chitosan:PEI wt ratio, 5:5) for 3 hours: Cys5.5 (A), DAPI (B), and overlay (C).

Results shown in FIG. 11 demonstrate that the 4M-NPs distributed throughout the cells, which indicated that endosomes were being disrupted and releasing the Cys5.5-4M-NPs into the cytoplasm. Furthermore, some 4M-NPs were observed in the nucleus.

Example 7

In Vitro MRI

In addition to determining whether the 4M-NPs could be used to deliver a gene-expressing plasmid, the 4M-NPs were also tested as an MRI contrast agent that would allow monitoring of the outcome of gene therapy. To determine whether 4M-NPs retained sufficient magnetism to be detectable by MRI, mag-micelles, 4M-NPs, and 4M-NPs:DNA complexes with chitosan:PEI wt ratio, 5:5 were analyzed by MR phantom imaging.

Various dilutions of mag-micelles, 4M-NPs (wt ratio, 5:5), 4M-NPs:DNA (weight ratio, 5:5:1) were diluted with deionized water. The concentrations of iron in the micelles were determined according to a protocol reported by Mykhaylyk [O. Mykhaylyk, et al., Nature Protocols 2007, 2, 2391]. 200 µl aliquots of various micelle solutions were added to a 96 well plate. MR images were obtained using an Agilent ASR 310 7 Tesla MRI high-field scanner. Multi-echo transverse relaxation experiments (MEMS) were performed in imaging mode to determine measure T2 values. Nonlinear least square fitting was performed in MATLAB (Mathworks, Inc) on a pixel-by-pixel basis. A region of interest (ROI) was drawn or each well, where the mean value was used to determine the transverse molar relaxivity r2. The image was recorded with Vnmrj 3.0.

Figure 12:
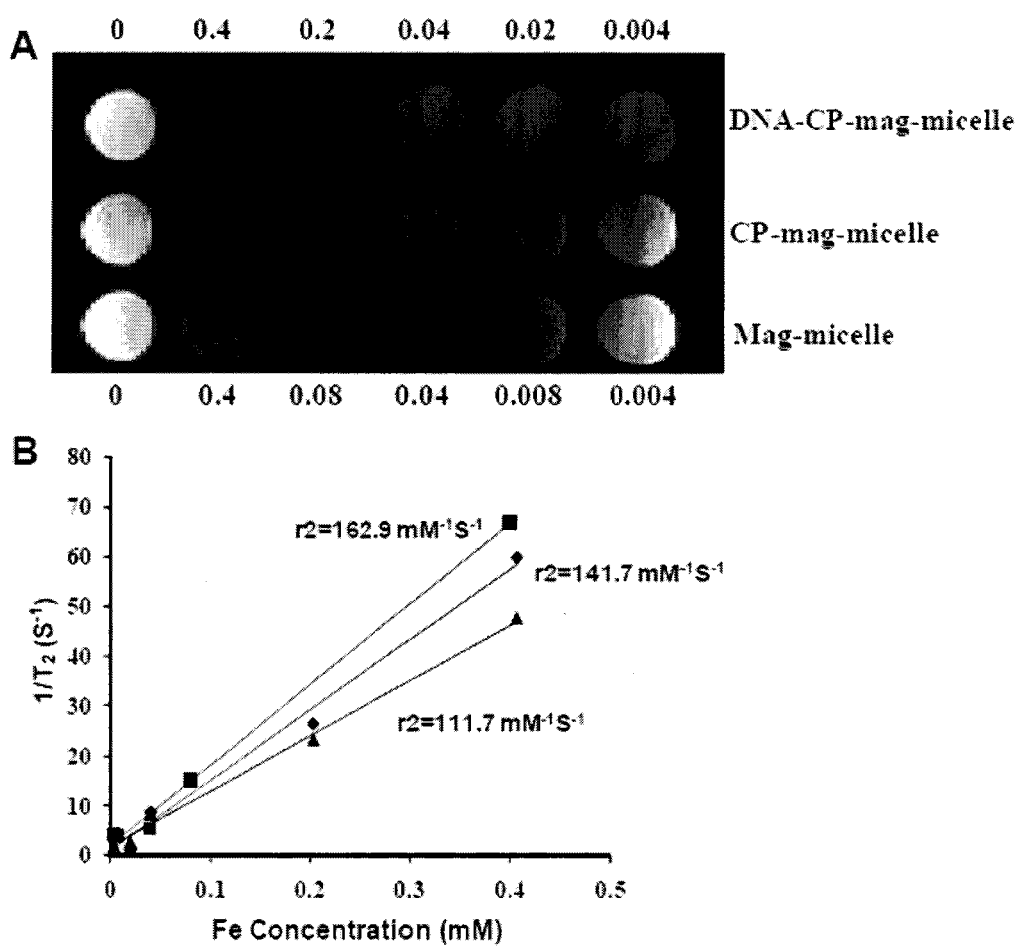
FIG. 12 shows magnetic properties of NPs: (A) T2-weighted MRI-images of mag-micelles, 4M-NPs (chitosan:PEI wt ratio, 5:5) and 4M-NPs:DNA (chitosan:PEI:DNA wt ratio, 5:5:1) (B) corresponding $R_2$ values of mag-micelles (■), 4M-NPs (▲), 4M-NPs:DNA (●).

FIGS. 12A and 12B showed the visual and quantitative contrast respectively, provided with various iron concentrations. The T2 relaxivity of mag-micelles (162.9 mM−1 S−1) were similar to 4M-NPs (141.7 mM−1 S−1) and 4M-NPs:DNA (111.7 mM−1 S−1) confirming that coating with cationic polymers did not alter magnetism significantly. These relaxitivity r2 values were significantly larger than those for SPION-dextran nanoparticles (30-50 Fe mM−1 S−1) [Y. X. J. Wang, et al., European Radiology 2001, 11, 2319] and Fe3O4-PEG-PAE (poly(b-amino ester) micelle (92.7 mM−1 s−1[G. H. Gao, et al., Small 2010, 6, 1201]). These r2 values were also comparable to the values of reported SPION micelles: 110.4 for folate-free SPION-DOXmicelles [31], 121.2 for PEG4.3 k-PCL7.2 k-SPION [D. Cheng, et al., Journal of Materials Chemistry 2011, 21, 4796], 207.99 Pluoronic-F127-SPION micelles [J. R. Lai, et al., Journal of Applied Physics 2010, 107].

Example 8

Biodistribution and Toxicity of 4M-NP In Vivo

Iron oxide nanoparticles coated with PEI-PEG-chitosan are considered safe for gene delivery [25]. However, 4M-NPs differ from the above particles by having (i) SPIONs in the core of the PEG-PLA micelle, which is expected to increase the plasma/tissue half-life of these particles, (ii) a modified composition of chitosan and PEI in the polymeric layer, and (iii) a novel method of preparation. These modifications necessitated determinations of the biodistribution, clearance and safety of 4M-NPs.

For biodistribution studies, mice were injected with 500 µl of 1 mg/ml Cys5.5-4M-NPs by i.p or i.v. In particular, fluorescent-labeled 4M-NPs were prepared by reacting Cys5.5-NHS with 4M-NP (wt ratio, 5:5) overnight. The Cys5.5-4M-NPs were purified by dialysis overnight in a dialysis membrane with molecular weight cutoff of 1K. 500 µl of Cys5.5-4M-NP solution containing 500 µg 4M-NP and 6.25 µg Cys5.5 was administered i.p or i.v. to C57BL/6 mice (6-8 week old). After 4 hours, the mice were euthanized via $CO_2$ asphyxiation. The organs were removed, weighted and scanned for fluorescence using the Xenogen IVIS imager (Caliper Life Sciences Inc, MA, USA).

Results are shown in FIG. 12A. The average Cy5.5 intensity of different organs obtained by photon emissions divided by the weight of organs was shown in FIG. 12B. Tissue binding was higher in spleen, liver and kidney than other tissues. Moreover, i.v. administration showed better tissue accumulation of NPs in all organs than i.p. administration, with the exception of the prostate tissue.

Figure 13:
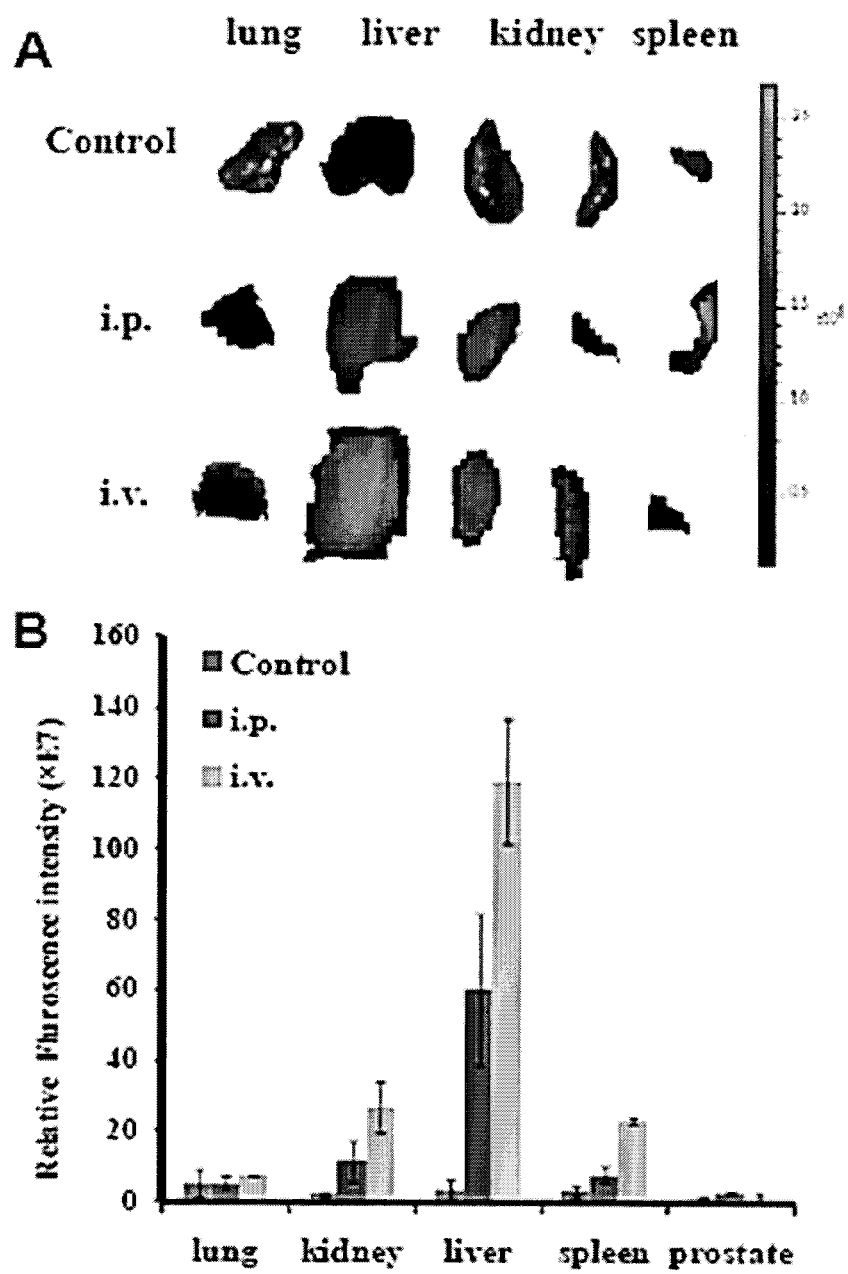
FIG. 13 shows biodistribution of Cy5.5 conjugated 4M-NPs in mice by Xenogen imaging. (A) Mice were administered with PBS (control) or Cy5.5-4M-NPs (1 μg/μl, 500 μl) by i.p (n=2) or i.v. Cy5.5-4M-NPs (5 μg/μl, 100 μl (n=2). Four hours after administration, fluorescence images of whole organs were acquired using the Xenogen imaging system. The spectrum gradient bar corresponds to the fluorescence intensity unit p/sec/cm2/sr. (B) Relative photons per mg organ weight is shown.

The in vivo toxicity of 4M-NPs was tested by H&E staining of paraffin fixed tissue sections 1, 2 and 7 days after i.p. administration of 4M-NP:DNA nanocomplexes (chitosan:PEI:DNA wt ratio, 5:5:1) in mice (n=6). FIG. 13 shows the H&E staining of liver 1, 2 and 7 days after i.p. administration. At the same time, Prussian blue staining was used to determine accumulation of iron particles inside the organs. Despite relatively high levels of NP accumulation in liver, spleen, lung and prostate which were confirmed by the presence of iron, no abnormalities in the histology of the organs were observed. Overall, the toxicity studies indicate that the 4M-NPs were well tolerated in mice.

Figure 14:
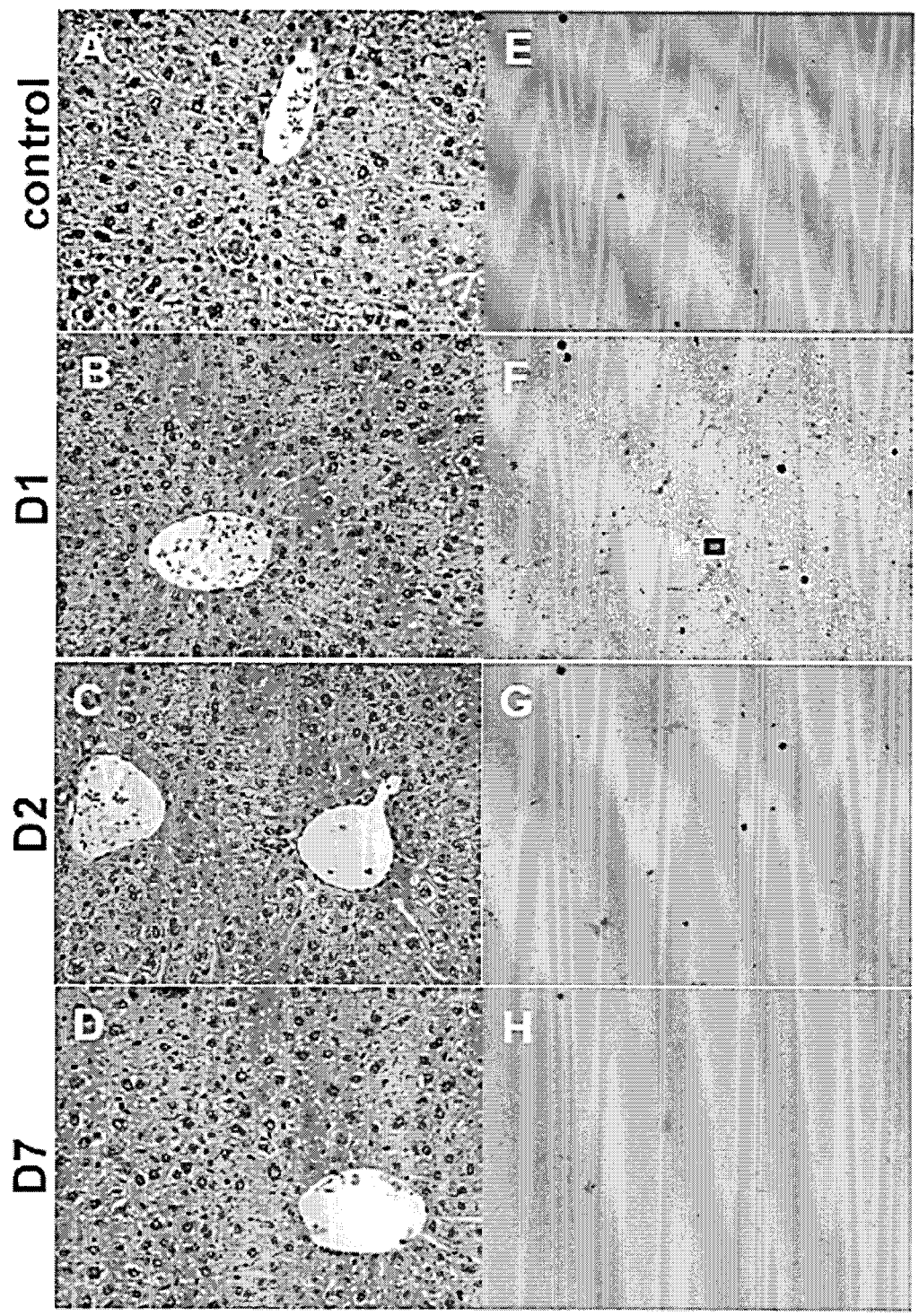
FIG. 14 shows H&E (A-D) and prussian blue staining of paraffin-fixed liver tissues: (A, E) control, (B, F) one day: D1, (C, G) two days: D2, (D, H) seven days: D7.
Figure 15:
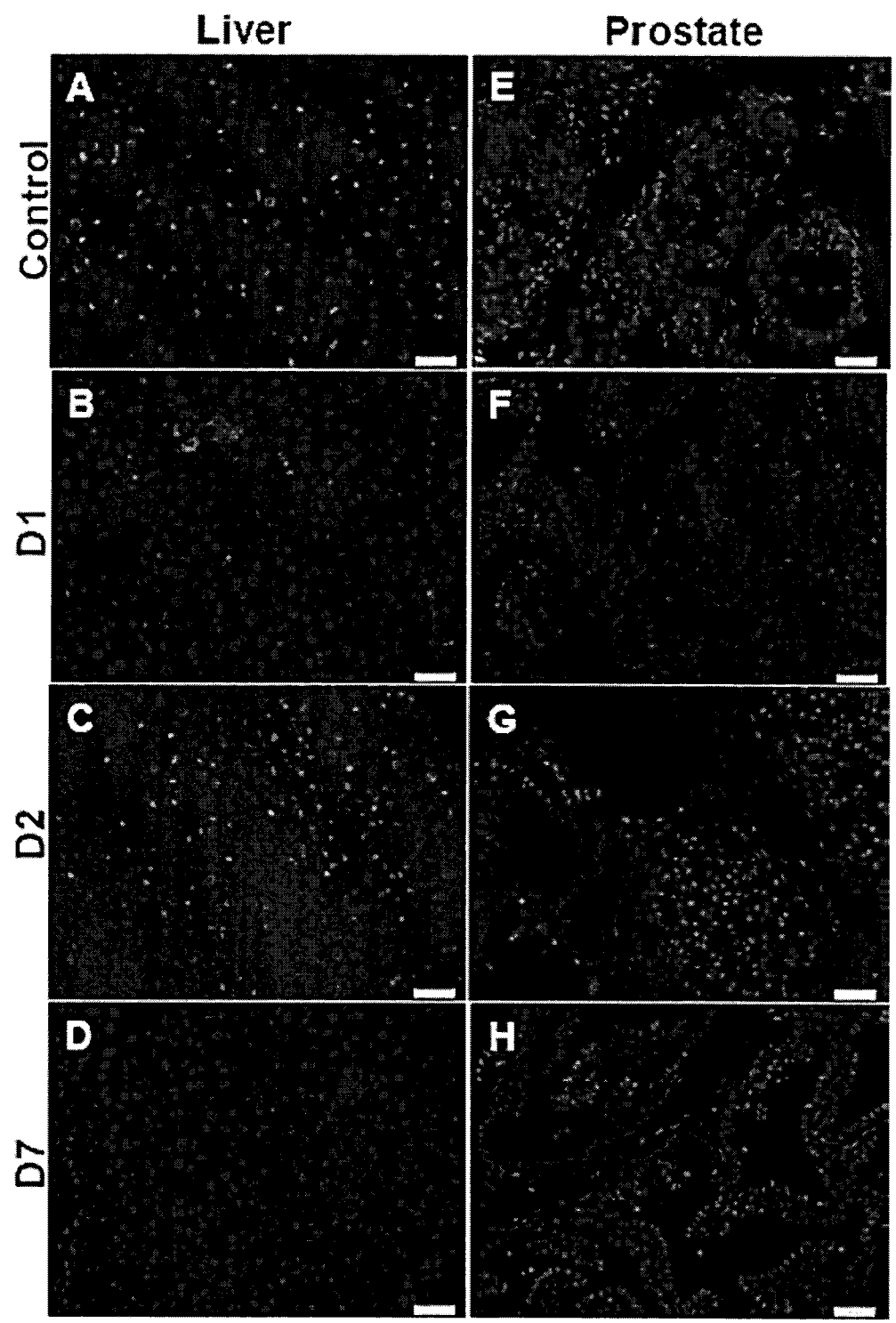
FIG. 15 shows tomato protein expression following in vivo gene transfection of 4M-NPs in liver (A-D) and prostate (E-H) tissues. Frozen sections were immunostained with anti-dsRed antibody and representative sections from each time points are shown. (A, E) control, (B, F) one day: D1, (C, G) two days: D2, (D, H) seven days: D7.
Figure 16:
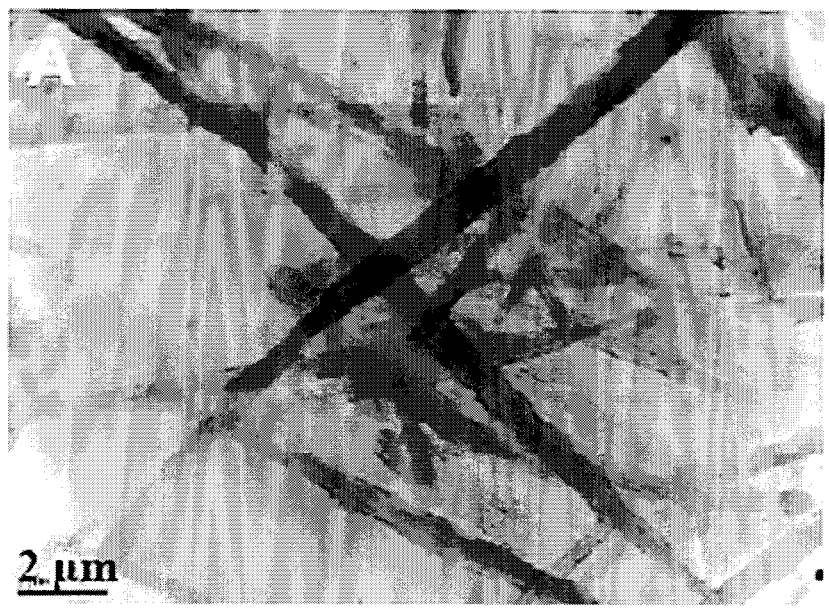
FIG. 16 shows SPION coated with oleic acid and oleylamine in hexane (A). (B) Higher magnification of (A).
Figure 16:
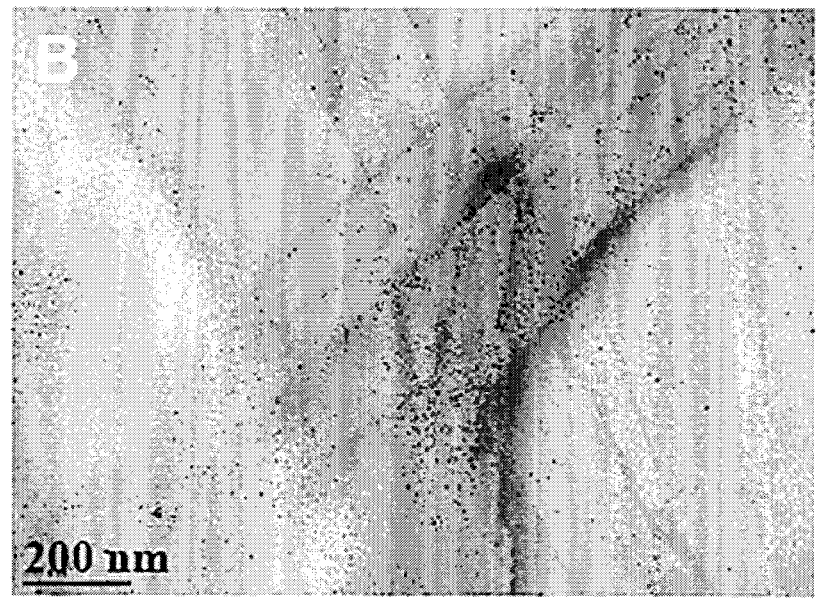
Figure 17:
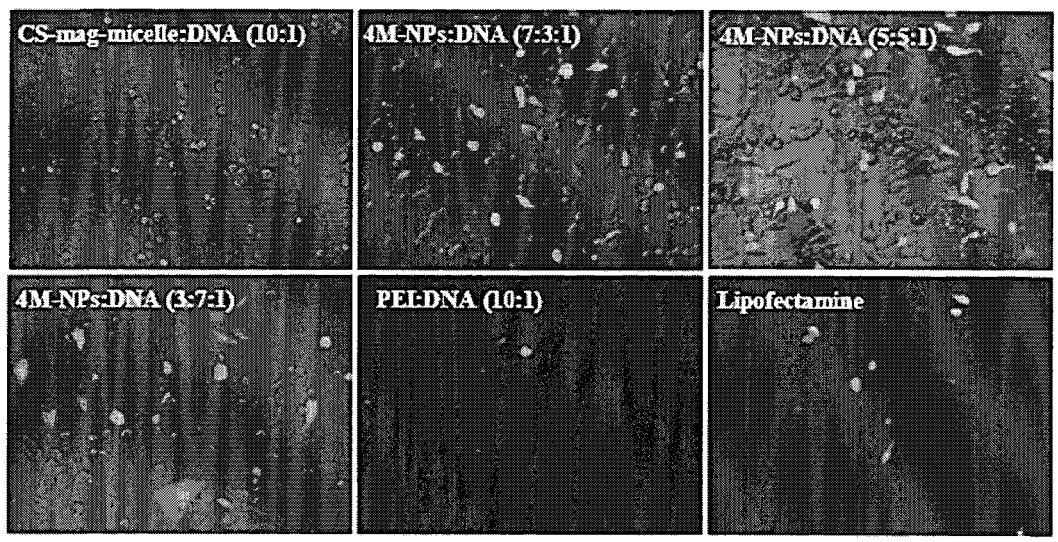
FIG. 17 shows cells were transfected with indicated NPs complexed with pCMV-td-tomato. Forty-eight hours after transfection, tomato protein expression was examined. Fluorescence images (100×) of PC3 cells transfected with 4M-NPs:DNA with different chitosan:PEI wt ratios.
Figure 18:
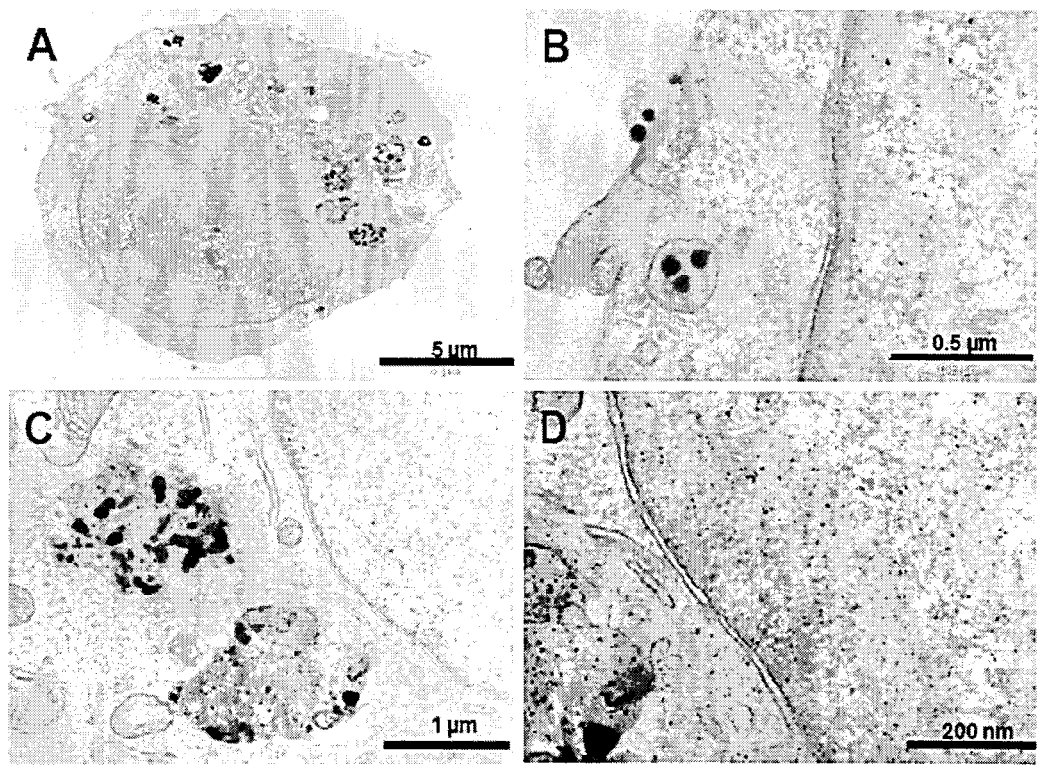
FIG. 18 shows TEM images showing uptake and intracellular distribution of 4M-NPs:DNA (chitosan:PEI:DNA wt ratio, 5:5:1) in HEK293 cells (A-D).

The intracellular SPIONs get degraded by the hydrolytic enzymes in lysosomes through low pH exposure, and iron ions are incorporated into the hemoglobin pool [P.-W. Lee, et al., Biomaterials 2010, 31, 1316; D. L. J. Thorek, et al., Annals of Biomedical Engineering 2006, 34, 23]. Accordingly, it was determined whether SPIONs were degraded following treatment with 4M-NPs:DNA complexes. Liver sections were stained with Prussian blue for iron detection. As shown in FIG. 14, positive Prussian blue staining was observed one day after i.p injection, which gradually decreased from day 2 to day 7. Very little Prussian blue staining was observed at day 7, indicating nearly complete degradation of SPIONs. These studies demonstrate that 4M-NPs are biocompatible and nontoxic, and can be cleared from tissues within one week.

Example 9

Gene Transfection Efficiency of 4M-NPs In Vivo

To evaluate the potential of 4M-NPs to deliver genes in vivo, 4M-NPs:DNA (chitosan:PEI:DNA wt ratio, 5:5:1) were administrated i.p. to male mice (n=6). After 1, 2 and 7 days, the mice receiving 4M-NP:DNA or PBS (control) were euthanized and the organs were collected. Tomato protein expression in the liver and prostate was observed by staining the frozen sections with anti-RFP and DAPI.

More particularly, 500 µl of 4M-NP:DNA (wt ratio, 5:5:1) containing 20 µg DNA or 500 µl PBS was administered i.p. to C57BL/6 mice (6-8 week old). After 1, 2 and 7 days, the mice were euthanized via $CO_2$ asphyxiation and liver, spleen, kidney, lung and prostate were removed and fixed in 10% formalin for hematoxylin and eosin (H&E) staining.

A part of the same organs was embedded in OCT freezing medium and kept at −80° C. until needed. The frozen tissues were sliced in 5 µm thick sections, fixed in 4% paraformaldehyde and stained using Prussian blue to indicate the presence of iron. For analysis of DNA expression, the 5 µm frozen sections were fixed with 4% paraformaldehyde and immunostained with anti-red fluorescent protein (RFP) and DAPI (nuclear DNA stain) (Vector Lab). All images were made using an Olympus BX51 microscope equipped with a DP-72 high-resolution digital camera (Olympus Imaging America Inc., Center Valley, Pa.).

Results are shown in FIG. 14. The 4M-NPs were able to deliver DNA as evidenced by the high tomato protein expression in the liver and prostate tissues of NP-treated mice. It is evident that gene expression started as early as day 1, increased on day 2, and continued up to day 7. Furthermore, the gene expression was not restricted to the edge of the tissue, but was seen distributed inside the organs.

Example 10

Transformation of Cells Expressing PSCA In Vivo with 4M-NPs

Prostate cancer is the second leading cause of cancer death among men in the United States. Currently, the best available systemic therapies for prostate cancer, including hormone therapy and the recently approved Taxotere (docetaxel), are not curative, and result only in an extension (sometimes modest) of survival. Moreover, both therapies are associated with significant morbidity and can have an adverse effect on the patient's quality of life. Better treatments are needed for aggressive forms of localized disease and hormone-refractory metastatic disease. In the long run, the best way to manage prostate cancer or other cancer is to detect it early and apply effective treatment as early as possible.

Prostate stem cell antigen (PSCA), a cell surface glycoprotein expressed in normal human prostate and bladder, is over-expressed in the majority of localized prostate cancer. Several studies have shown that the increased PSCA expression is correlated with the occurrence of prostate cancer, and then the PSCA has been used as a marker for human cancer diagnosis. Olafsen et al. developed the magnetic NPs coupled with PSCA antibody (PSCA-Ab) on the surface for targeting and imaging to prostate cancer tissues in vivo [Olafsen, T. et al., Journal of Immunotherapy, 2007, 30:396-405].

Provided herein are methods wherein 4M-NPs were prepared as described above. PSCA antibody targeted 4M-NPs particles were prepared and the cell uptake of PSCA-4M-NPs was tested on mouse prostate cancer cells. The MRI and gene transfection efficiency of PSCA-4M-NPs were tested in a TRAMP mouse model of prostate cancer.

More particularly, 4M-NPs were conjugated with prostate stem cell antigen (PSCA) antibody and modified with Cy5.5. In vitro uptake of nanoparticles were evaluated by confocal microscopy. In vivo MRI was done using Agilent ASR 310 7 Tesla MRI high-field scanner. In vivo gene delivery was visualized by fluorescent microscopy 48 hours after i.v. administration.

FIG. 19 shows that PSCA antibody (PSCA-Ab) conjugated 4M-NPs demonstrated much higher cellular uptake and transfection efficiency than 4M-NPs without PSCA-Ab. In vivo MRI of prostate cancer mice showed contrast enhancement starting from 7.7 min post i.v. injection of PSCA-4M-NPs. Moreover, i.v. administration of PSCA-Ab-4M-DNA NPs expressed encoded tomato protein (Ptd) with high efficiency in the prostate tumors of TRAMP mice at 48 hours. These results demonstrate that PSCA-Ab-4M-NPs can target delivery of genes for prostate cancer and enhance MRI contrast.

To optimize the amount of PSCA-Ab on the surface of NPs, NPs were modified with Cy5.5 by reacting the Cy5.5-NHS with 4M-NPs. 3 microgram of different Cy5.5-PSCA-Ab (0, 0.25 wt %, 0.5 wt %, 1 wt %)-4M-NPs were added to TRC cells in 8 well-chamber in duplicate. Three hours after NPs incubated with TRC cells, the cells were fixed and stained with DAPI. The distribution of nanoparticles inside the cells was imaged with the multiphoton Olympus BX61W1 confocal microscope.

FIG. 20 shows confocal images which demonstrate that 1% PSCA-Ab-4M-NPs shows the highest binding affinity to the TRAMP mouse prostate cancer cells (TRC) compared to the 4M-NPs, 0.25 wt % or 0.5 wt % PSCA-Ab-4M-NPs.

In order to determine whether MRI could be used to monitor delivery of the contrast agent and a gene encapsulated in the 4M-NPs to the prostate cancer, the following procedures were performed. A TRAMP mouse was anesthetized with 3% isoflurane. A non-metallic catheter was inserted into the tail-vein which was comprised of one 60 µl volume section (preloaded with saline) and one 140 µl section which was placed outside of the MRI and preloaded with nanoparticles. Respiration and temperature of the mouse were monitored with small animal monitoring system equipped with a fiber optic thermometer and feedback control (SA Instruments, Inc). After acquiring scout images, in vivo T2-weighted fast spin echo images (FSEMS) were acquired with an acquisition bandwidth of 100 kHz, TR-3450 ms, a TE=72.00 ms, and fat suppressed. The data were collected with a matrix size of 256×256, a field of view (FOV) of 45×90 mm2, 21 coronal slices, 2 dummy scans and 2 averages. These images were arrayed and run consecutively through the course of the injection up to 80 minutes to observe intensity changes within the tumor, which were characterized within VnmrJ 3.1. FIG. 21 provides these images, and demonstrates that a PSCA-Ab-4M-NPs-DNA complex delivered the SPIO contrast agent and was targeted to prostate cancer in 7.7 min after i.v. administration. The amount of particles increased with time.

Figure 22:
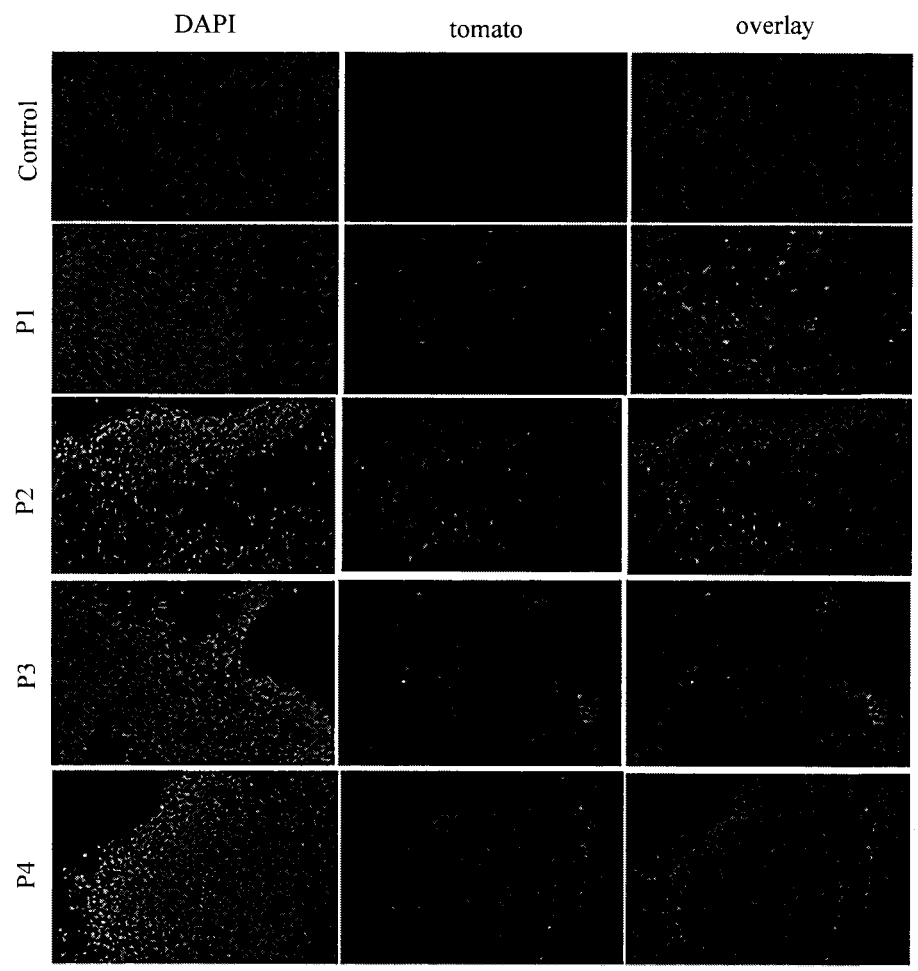
FIG. 22 shows in vivo gene transfection in TRAMP mice.

Finally, to test the gene transfection efficiency of PSCA-Ab-4M-DNA in prostate cancer after the MRI, the following procedures were followed. Forty eight hours after i.v. administration of the PSCA-Ab-4M-DNA, the mouse was euthanized via $CO_2$ asphyxiation and prostate tumor was excised. To determine whether PSCA-Ab-4M-DNAs delivered the payload deep within the tumor, tumor tissue was sliced into 4 pieces, as shown in FIG. 22, snap frozen in OCT and kept at −80° C. Frozen sections were immunostained with anti-red fluorescent protein (RFP) and DAPI (nuclear DNA stain) (Vector Lab) and examined using an Olympus BX51 microscope equipped with a DP-72 high-resolution digital camera (Olympus Imaging America Inc., Center Valley, Pa.). FIG. 22 shows that tomato protein expression was seen throughout the entire tumor.

The invention claimed is:

1. A composition comprising a micelle having a hydrophobic superparamagnetic iron oxide nanoparticle (SPION) core, a first coating comprising a cationic polymer, and a second coating comprising a polynucleotide wherein the first coating comprises chitosan and polyethyleneimine (PEI), and wherein chitosan has a chemical formula of I:

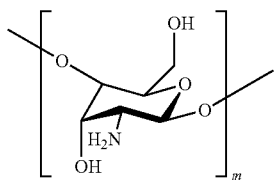

wherein "m" is between 1 and 10,000; and wherein PEI has a chemical formula of II:

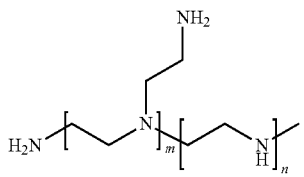

wherein "m" is between 1 and 10,000, and "n" is between 1 and 10,000.

2. The composition of claim 1, wherein the micelle comprises multiple copolymers having the chemical formula of:

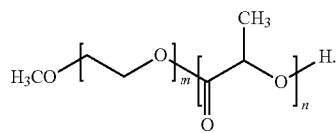

wherein "m" is between 1 and 10,000, "n" is between 1 and 10,000.

3. The composition of claim 2, wherein the SPION core comprises a coating of oleic acid and oleylamine.

4. The composition of claim 3, wherein the SPION core is prepared using iron, 1,2-dodecanediol, oleic acid, oleylamine, and benzyl ether.

5. The composition of claim 2, wherein a molar weight ratio of chitosan and polynucleotide is between approximately 3:1 and 7:1.

6. The composition of claim 5, wherein the polynucleotide is at a concentration between approximately 1 and 3 µg/ml.

7. The composition of claim 2, wherein a molar weight ratio of PEI and polynucleotide is between approximately 7:1 and 3:1.

8. The composition of claim 7, wherein the polynucleotide is at a concentration between approximately 1 and 3 µg/ml.

9. The composition of claim 2, wherein a molar weight ratio of chitosan and PEI is between approximately 3:7 and 7:3.

10. The composition of claim 9, wherein a molar weight ratio of chitosan and PEI is approximately 5:5.

11. The composition of claim 10, wherein a molar weight ratio of chitosan, PEI and polynucleotide is approximately 5:5:1.

12. The composition of claim 11, wherein the polynucleotide is at a concentration between approximately 1 and 3 µg/ml.

13. The composition of claim 1, further comprising a ligand.

14. The composition of claim 13, wherein in the ligand is an antibody.

15. The composition of claim 14, wherein the antibody is specific for a prostate stem cell antigen.

16. A method of transfecting a cell with a polynucleotide comprising, contacting the cell with a composition of claim 1.

17. The method of claim 16, wherein the micelle comprises multiple copolymers having the chemical formula of III:

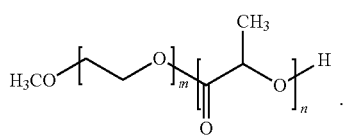

wherein "m" is between 1 and 10,000, "n" is between 1 and 10,000.

18. The method of claim 16, further comprising placing a magnet proximal to the cell.

19. The method of claim 16, further comprising transforming the cell.

20. The method of claim 17, wherein a molar weight ratio of chitosan and PEI is approximately 5:5.

21. The method of claim 20, wherein a molar weight ratio of chitosan, PEI and polynucleotide is approximately 5:5:1.

22. The method of claim 21, wherein the polynucleotide is at a concentration between approximately 1 and 3 µg/ml.

23. The method of claim 16, wherein the cell is in vivo.

24. The method of claim 23, wherein the composition further comprises a cancer cell ligand and the cell is a cancer cell.

25. The method of claim 24, wherein the cancer cell ligand is an antibody specific for prostate stem cell antigen.

26. The method of claim 16, further comprising the step of detecting transfection of the cell using magnetic resonance imaging.

27. The method of claim 23, further comprising the step of detecting transfection of the cell using magnetic resonance imaging.

28. A composition comprising a micelle having a hydrophobic superparamagnetic iron oxide nanoparticle (SPION) core, a first coating comprising a cationic polymer, and a second coating comprising a polynucleotide, wherein the first coating comprises polyethyleneimine and chitosan, wherein the chitosan has a chemical formula of:

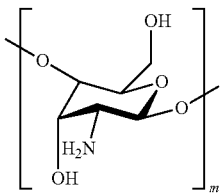
(I.)

wherein "m" is between 1 and 10,000;
and wherein PEI has a chemical formula of:

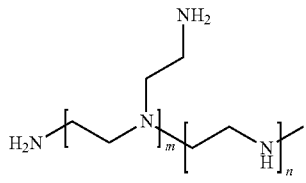
(II.)

wherein "m" is between 1 and 10,000, and "n" is between 1 and 10,000, wherein the micelle further comprises multiple co-polymers having the chemical formula of:

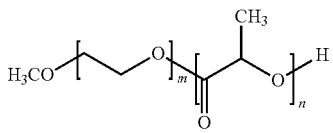
(III.)

wherein "m" is between 1 and 10,000, "n" is between 1 and 10,000, wherein the molar weight ratio of chitosan and polynucleotide is between approximately 3:1 and 7:1, the molar weight ratio of PEI and polynucleotide is between approximately 7:1 and 3:1, and the molar weight ratio of PEI to chitosan is between approximately 3:7 and 7:3.

29. The composition of claim 28, wherein a molar weight ratio of chitosan, PEI and polynucleotide is approximately 5:5:1.

30. The composition of claim 28, wherein the polynucleotide is at a concentration between approximately 1 and 3 μg/ml.

* * * * *

UNITED STATES PATENT AND TRADEMARK OFFICE
CERTIFICATE OF CORRECTION

PATENT NO. : 9,439,978 B2
APPLICATION NO. : 14/346330
DATED : September 13, 2016
INVENTOR(S) : Subhra Mohapatra et al.

Page 1 of 1

It is certified that error appears in the above-identified patent and that said Letters Patent is hereby corrected as shown below:

IN THE SPECIFICATION

At column 1, lines 21-24, delete

"This invention was made with government support under the National Institutes of Health Grants R41CA139785 and 5R01CA152005. The U.S. government has certain rights in this invention."

and replace with

--This invention was made with government support R41 CA139785 and R01 CA152005 awarded by the National Institutes of Health. The Government has certain rights to the invention.--

Signed and Sealed this
Fifteenth Day of November, 2016

Michelle K. Lee
*Director of the United States Patent and Trademark Office*